United States Patent [19]
Franke et al.

[11] Patent Number: 6,013,429
[45] Date of Patent: Jan. 11, 2000

[54] PHOTOGRAPHIC ELEMENT WITH NEW SINGLET OXYGEN QUENCHERS

[75] Inventors: Catherine A. Franke; Albert J. Mura, Jr., both of Rochester; Shari L. Eiff, Rush, all of N.Y.

[73] Assignee: Eastman Kodak Company, Rochester, N.J.

[21] Appl. No.: 09/032,555

[22] Filed: Feb. 27, 1998

[51] Int. Cl.$^7$ ............................. G03C 7/30; G03C 7/333
[52] U.S. Cl. ...................... 430/551; 430/607; 430/613
[58] Field of Search ..................... 430/551, 607, 430/613

[56] References Cited

U.S. PATENT DOCUMENTS

| | | | |
|---|---|---|---|
| 3,336,135 | 8/1967 | Terashima et al. | 430/551 |
| 4,483,918 | 11/1984 | Sakai et al. | 430/372 |
| 4,795,696 | 1/1989 | Sasaki et al. | 430/512 |
| 4,839,264 | 6/1989 | Kida et al. | 430/551 |
| 4,880,733 | 11/1989 | Kaneko | 430/551 |
| 5,017,465 | 5/1991 | Nishijima | 430/551 |
| 5,082,766 | 1/1992 | Nishijima et al. | 430/551 |
| 5,139,931 | 8/1992 | Seto et al. | 430/551 |
| 5,200,309 | 4/1993 | Merkel et al. | 430/546 |
| 5,208,140 | 5/1993 | Nishijima | 430/551 |
| 5,236,819 | 8/1993 | Kadokura et al. | 430/551 |
| 5,415,989 | 5/1995 | Wolff et al. | 430/551 |
| 5,484,696 | 1/1996 | Jain et al. | 430/551 |
| 5,491,054 | 2/1996 | Jain et al. | 430/551 |
| 5,561,037 | 10/1996 | Jain et al. | 430/551 |
| 5,565,312 | 10/1996 | Jain | 430/551 |

FOREIGN PATENT DOCUMENTS

| | | |
|---|---|---|
| 0 457 543 A1 | 11/1990 | European Pat. Off. . |
| 0 486 216 A1 | 5/1992 | European Pat. Off. . |
| 95/22082 | 2/1994 | WIPO . |

OTHER PUBLICATIONS

Y. Kaneko et al, The Light Stabilizing Effect of Combined Usage of Two Stabilizers Observed in Color Paper, 1993, IS&T's 46th Annual Conf. pp. 299–302.

Y. Kaneko, Development of New Generation Color Couplers and Image Stabilizers Introduced in Konica Color Print Papers over the Last Decade, 1993, Nippon Shashin Gakkai-shi, vol. 56, No. 4, pp. 301–308.

*Primary Examiner*—Richard C. Schilling
*Assistant Examiner*—Amanda C. Walke
*Attorney, Agent, or Firm*—Andrew J. Anderson

[57] ABSTRACT

Photographic elements are disclosed comprising a silver halide emulsion layer having associated therewith a magenta coupler and a magenta dye stabilizer compound of the formula S-I:

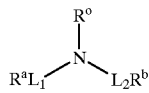

wherein $R^o$ represents an aryl group or a heterocyclic group; $L_1$ and $L_2$ are independently linear alkylene or cycloalkylene linking groups; and $R^a$ and $R^b$ are independently selected substituent groups at least one of which has a σ* value of at least 1.8. Compounds in accordance with formula S-I act as singlet oxygen quenchers and are effective stabilizers for magenta dye images. Photographic elements of the present invention upon exposure and photographic processing yield magenta dye images that have low fading when exposed to light.

19 Claims, 1 Drawing Sheet

PHOTOGRAPHIC ELEMENT WITH NEW SINGLET OXYGEN QUENCHERS

FIELD OF THE INVENTION

This invention relates to photographic elements containing a layer having associated therewith magenta dye forming couplers and compounds which reduce fading of the dyes formed from the couplers on processing of the photographic element.

BACKGROUND OF THE INVENTION

In a silver halide photographic element, a color image is formed when the element is exposed to light and then subjected to color development with a primary aromatic amine developer. Color development results in imagewise reduction of silver halide and production of oxidized developer. Oxidized developer reacts with one or more incorporated dye-forming couplers to form an imagewise distribution of dye.

The dyes that are formed by any color coupler during processing have a tendency to fade over time as a result of exposure to light, heat, humidity and oxygen. As all three image dyes of a typical color element fade, this results in overall fading of the image over time. In addition, since the three image dyes may not fade at the same rate, an apparent change in image color may result. Such change is particularly noticeable in the case of magenta image dye fading.

A significant disadvantage of many magenta dye-forming couplers is fading of the dyes formed from them by photographic processing due to extended exposure to low levels of light. Compounds which are included in photographic elements to reduce image dye fading are known as stabilizers. Inclusion of stabilizers in color photographic materials can reduce the deterioration of the dye images which occurs over time as a result of the action of light, heat, humidity and/or oxygen. This is especially true for dyes formed from pyrazoloazole couplers. U.S. Pat. Nos. 5,236,819, 5,082,766 and 5,017,465 and German Published Patent Application DTOS 4,307,194, e.g., describe the use of certain stabilizers with pyrazoloazole couplers to improve their dye stability. One class of stabilizers which is disclosed includes compounds of the following structure:

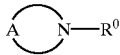

wherein A represents a group of non-metal atoms necessary to complete a 5-membered to 8-membered nitrogen-containing ring and $R^0$ represents an aryl group or a heterocyclic group. Preferred compounds of such formula as described in U.S. Pat. No. 5,017,465 include compounds wherein A represents the atoms necessary to complete a thiomorpholine 1,1-dioxide group and where $R^0$ represents an alkoxy substituted phenyl group. Such compounds are believed to stabilize by acting as singlet oxygen quenchers.

It would be desirable to improve the light stability of dyes derived from magenta dye forming couplers, and thus retain the color rendition of the image for a longer period of time. It would also be desirable to provide singlet oxygen quenching stabilizers with greater structural flexibility than the prior art stabilizers comprising nitrogen-containing ring structures, so that other properties of such compounds may be more easily adjusted where desired (e.g., compound solubility and dispersibility).

SUMMARY OF THE INVENTION

In accordance with one embodiment of the invention, a photographic element is disclosed comprising a silver halide emulsion layer having associated therewith a magenta coupler and a magenta dye stabilizer compound of the formula S-I:

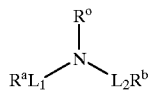

wherein $R^0$ represents an aryl group or a heterocyclic group;

$L_1$ and $L_2$ are independently linear alkylene or cycloalkylene linking groups; and $R^a$ and $R^b$ are independently selected substituent groups at least one of which has a $\sigma^*$ value of at least 1.8.

In accordance with preferred embodiments, $R^0$ represents a substituted phenyl group of the following formula:

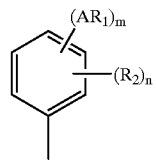

wherein m is 1, 2, 3 or 4;

n is 0, 1, 2, 3, or 4, provided that the sum of m and n is less than or equal to 5;

A is $-NR_1'-$, $-S-$, or $-O-$; and $R_1$ and $R_1'$ are independently H or a substituent group and $R_2$ is a substituent group, provided that substituent groups represented by $R_1$ and $R_2$ or two $R_1$ or $R_2$ groups may be joined to form a ring.

In accordance with most preferred embodiments, $R^0$ represents a para-substituted phenyl group of the formula:

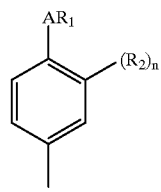

where n is 0 or 1.

Compounds in accordance with formula S-I act as singlet oxygen quenchers and are effective stabilizers for magenta dye images. Photographic elements of the present invention upon exposure and photographic processing yield magenta dye images that have low fading when exposed to light.

DETAILED DESCRIPTION OF THE INVENTION

Figure 1:
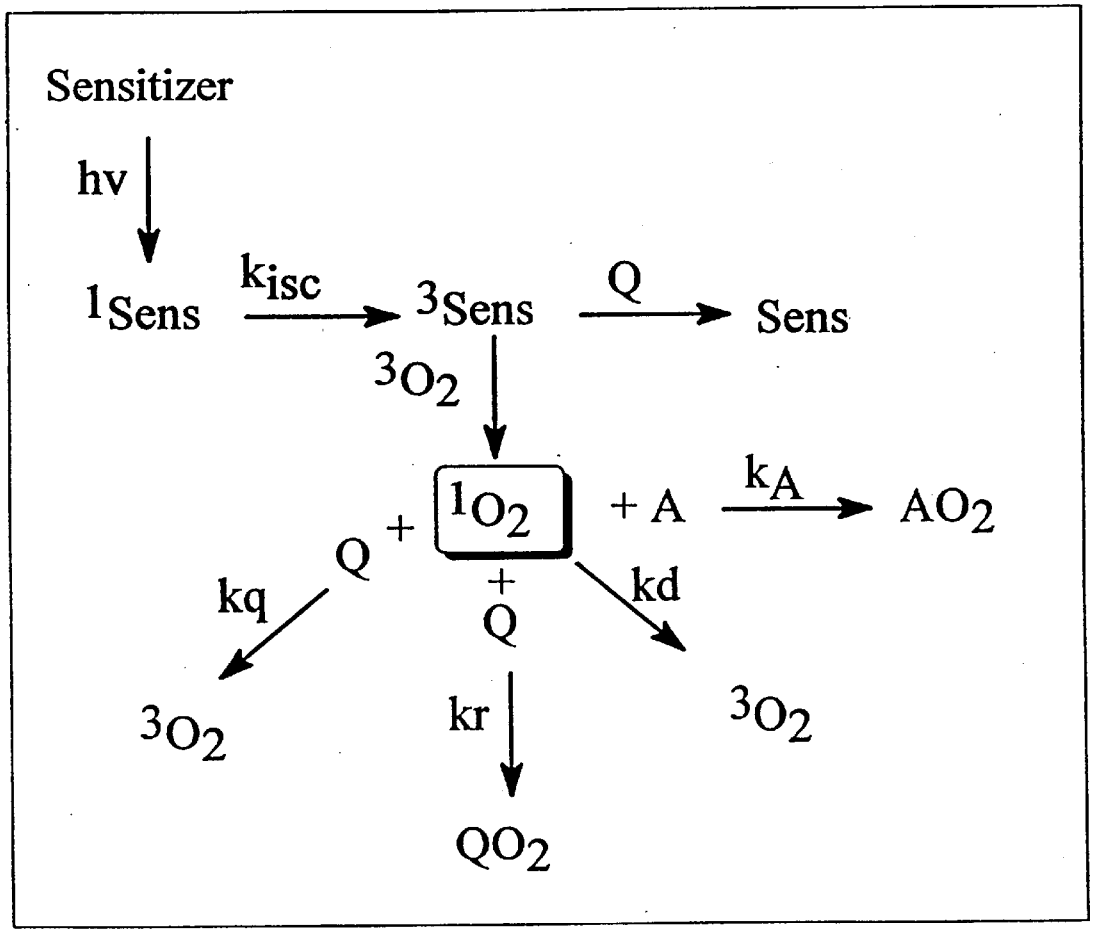
FIG. 1 illustrates a general scheme for the photooxidation of an acceptor compound in the presence of a singlet oxygen quencher compound.

As used herein, unless otherwise indicated the alkyl and aryl groups, and the alkyl and aryl portions of groups, can be unsubstituted or substituted with non-interfering substituents. Typical alkyl groups have 1 to 32 carbon atoms and typical aryl groups have 6 to 32 carbon atoms. Depending upon the position of the group, preferred alkyl groups can have 1 to 20 carbon atom, 1 to 12 carbon atoms or 1 to 4 carbon atoms and preferred aryl groups can have 6 to 20 or 6 to 10 carbon atoms. Other groups identified below which contain a replaceable hydrogen atom can be substituted or not, depending on the particular structure and properties desired.

$R^0$ represents an aryl or heterocyclic group. Representative groups include phenyl, 1-naphthyl, 2-furyl and 2-thienyl, and pyridyl. In a preferred embodiment, $R^0$ represents a substituted phenyl group represented by the formula:

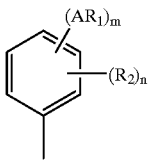

wherein m is 1, 2, 3 or 4; n is 0, 1, 2, 3, or 4, provided that the sum of m and n is less than or equal to 5; A is —$NR_1'$—, —S—, or —O—; and $R_1$ and $R_1'$ are independently H or a substituent group and $R_2$ is a substituent group, provided that substituent groups represented by $R_1$ and $R_2$ or two $R_1$ or $R_2$ groups may be joined to form a ring.

$R_1$ preferably represents an alkyl group, a cycloalkyl group, an alkenyl phenyl group, an aryl group, a heterocyclic group, a bridged hydrocarbon group, an alkyl sulfonyl group or an aryl sulfonyl group. For $R_1$, the alkyl group may include, e.g., a straight-chain or branched-chain alkyl group having 1 to 24 carbon atoms; the cycloalkyl group, e.g., a cycloalkyl group having 5 to 24 carbon atoms; the alkenyl group, e.g., an alkenyl group having 3 to 24 carbon atoms; the aryl group, e.g., a phenyl group and naphthyl group; the heterocyclic group, e.g., a pyridyl group, an imidazolyl group and a thiazole group; the acyl group, e.g., an acetyl group and a benzoyl group; the bridged hydrocarbon group, e.g., a bicyclo[2.2.1]heptyl group, etc., respectively. $R_2$ may represent, e.g., a halogen atom or the groups such as alkyl, aryl, alkoxy, aryloxy, alkythio, arylthio, acyl, alkoxycarbonyl, carbamoyl (e.g., alkylcarbamoyl, arylcarbamoyl) ureido (e.g., alkylureido, arylureido), sulfamoyl (e.g., alkylsufamoyl, arylsulfamoyl), amino, alkylsulfonyl, arylsulfonyl, nitro, cyano and carboxy.

The —$AR_1$ substituent in the above formula is preferably located para to the amino substituent, and the —$R_2$ substituent (when present) is preferably located ortho to the —$AR_1$ substituent. In accordance with particularly preferred embodiments, $R^0$ thus is represented by the formula:

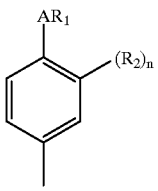

wherein n represents 0 or 1.

$L_1$ and $L_2$ are independently linear alkylene or cycloalkylene linking groups. $L_1$ and $L_2$ preferably are selected from alkylene groups having the formula —$(C(R)(R))_p$—, where p equals from 1 to 6, more preferably from 1 to 3, and most preferably 2, and each R may be independently H or an alkyl group, or two alkyl groups may be joined to form a cycloalkylene ring. Examples of cycloalkylene ring linking groups include the following:

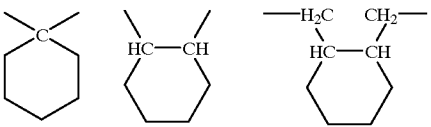

Most preferably, each of $L_1$ and $L_2$ represents an unsubstituted ethylene linking group.

$R^a$ and $R^b$ are independently selected substituent groups at least one of which, and more preferably each of which, has a σ* value of at least 1.8. Preferably, at least one of $R^a$ and $R^b$ has a σ* value of at least 2.5, and more preferably each of $R^a$ and $R^b$ has a σ* value of at least 2.5. The Taft σ* constant is described in *pK$_a$ Prediction for Organic Acids and Bases*, D. Perrin, B. Dempsey, and E. Serjeant, Chapman and Hall, New York, N.Y.(1981). It represents the electronic effect of a substituent in an aliphatic system. Values for various substituents may be found in Appendix Table A-1 of the above publication. Additional values may be found in "Exploring QSAR—Hydrophobic, Electronic, and Steric Constants," C. Hansch, A. Leo, and D. Hoekman, ACS Professional Reference Book, ACS, Washington, D.C., 1995. Hydrogen has a σ* value of +0.49 and methyl has a value of 0.0. While a σ* value of at least 1.8, and more preferably at least 2.5 is preferred for each of $R^a$ and $R^b$ in order to provide effective singlet oxygen quenching and good stabilizer compound stability towards singlet oxygen ($^1O_2$) when used in accordance with the invention, combined σ* values for $R^a$ and $R^b$ above 7.2 may result in lower than desired compound stability and singlet oxygen quench rates. Preferred combined σ* values for $R^a$ and $R^b$ for compounds used in accordance with the invention are accordingly from 3.6 to 7.2, and more preferably 4.5 to 6.0, in order to provide effective singlet oxygen quenching and good stabilizer compound stability towards singlet oxygen.

The σ* constant value of a substituent may be determined by reference to the tables of the above publications. Table A.2 in the above *pK$_a$ Prediction for Organic Acids and Bases* reference contains a compilation of published Taft equations, in which various parent compounds (acids or bases) are utilized. As an alternative, one may determine the value experimentally from the formula:

$$\sigma^* = (pK^O - pK)/\rho^*$$

where ρ* is the reaction constant which is the slope of the straight line plot of pK$^O$–pK versus σ* for known substituents of the base compound where pK$^O$ is the ionization constant of the base compound at 25° C., and pK is the ionization constant of the substituted compound at 25° C., which may be determined experimentally in accordance with conventional techniques. ρ* may be determined from the slope of the linear plot of (pK$^O$–pK) vs. σ* values experimentally determined or from Table A.2 of the above publication. Reference may also be made to *Mechanism and Theory in Organic Chemistry*, 3rd Ed, T. H. Lowry and K. S. Richardson, Harper and Row, New York, (1987).

Desirably, at least one of $R^a$ and $R^b$ is an electron withdrawing group selected from sulfamoyl, sulfonyl, sulfinyl, phosphonyl, phosphinyl, perfluorinated alkyl, and perfluorinated thio groups. More preferably at least one of and most preferably each of $R^a$ and $R^b$ is of the formula:

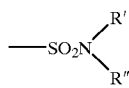

wherein R' and R" are independently selected from the group consisting of H, alkyl and aryl groups or together form a cyclic ring. The σ* value of various preferred substituents are listed below, as reported in the "Exploring QSAR—Hydrophobic, Electronic, and Steric Constants" reference cited above:

| Substituent | σ* |
|---|---|
| —CF$_3$ | 2.61 |
| —CF$_2$CF$_2$CF$_2$CF$_3$ | 2.44 |
| —CN | 3.64 |
| —OCHF$_2$ | 2.81 |
| —PO(OEt)$_2$ | 3.02 |
| —PO(Bu)$_2$ | 2.81 |
| —SO$_2$NMe$_2$ | 2.65 |
| —SO$_2$NH$_2$ | 2.61 |
| —SCF$_3$ | 2.75 |
| —SCN | 3.43 |
| —SOPh | 3.08 |
| —SOMe | 2.88 |
| —SO$_2$Ph | 3.25 |
| —SO2Me | 3.68 |
| —N(Me)SO$_2$CF$_3$ | 3.0 |
| —NHSO$_2$CF$_3$ | 3.1 |
| —NCS | 2.65 |
| —N(SO$_2$Me)$_2$ | 2.80 |
| —N(CH$_2$CH$_2$OH)$_2$ | 2.43 |

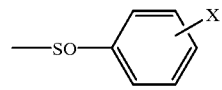

| X | |
|---|---|
| p-Me | 3.02 |

| Substituent | σ* |
|---|---|
| p-Br(Cl) | 3.14 |
| p-t-Bu | 2.97 |

—SO$_2$—⟨aryl⟩—X

| X | |
|---|---|
| p-Br | 3.35 |
| p-Cl | 3.49 |
| p-F | 3.4 |
| p-Me | 3.32 |
| p-t-Bu | 3.23 |
| p-OMe | 3.23 |

—O—⟨aryl⟩—X

| X | |
|---|---|
| p-CN | 2.73 |
| o-CN | 2.67 |
| m-CN | 2.59 |
| p-Br | 2.44 |
| o-Br | 2.48 |
| m-Br | 2.48 |
| p-Cl | 2.69 |
| o-Cl | 2.62 |
| p-F | 2.44 |
| m-F | 2.51 |
| p-SO$_2$Me | 2.85 |

Specific stabilizer compounds of formula S-I which may be used within the scope of the present invention include the following structures:

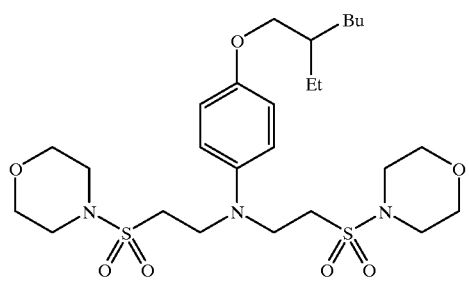

S-I-1

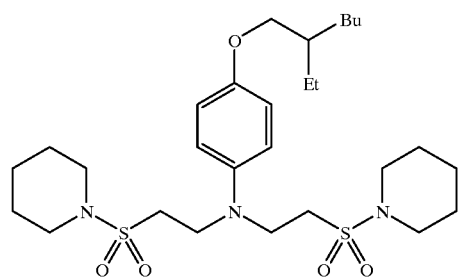

S-I-2

S-I-3
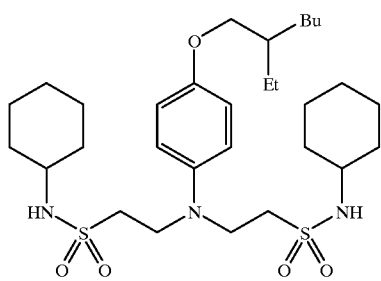
S-I-4
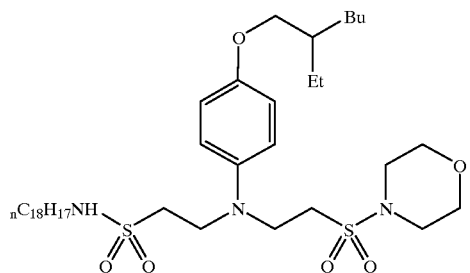
S-I-5
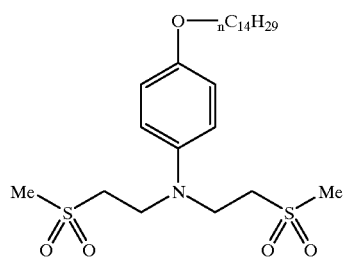
S-I-6
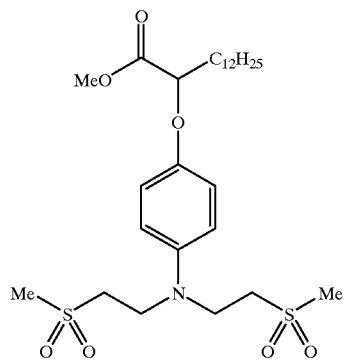
S-I-7
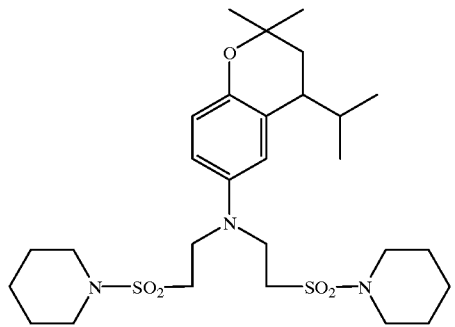

-continued
S-I-8
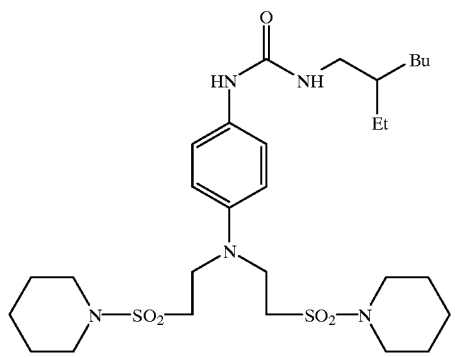
S-I-9
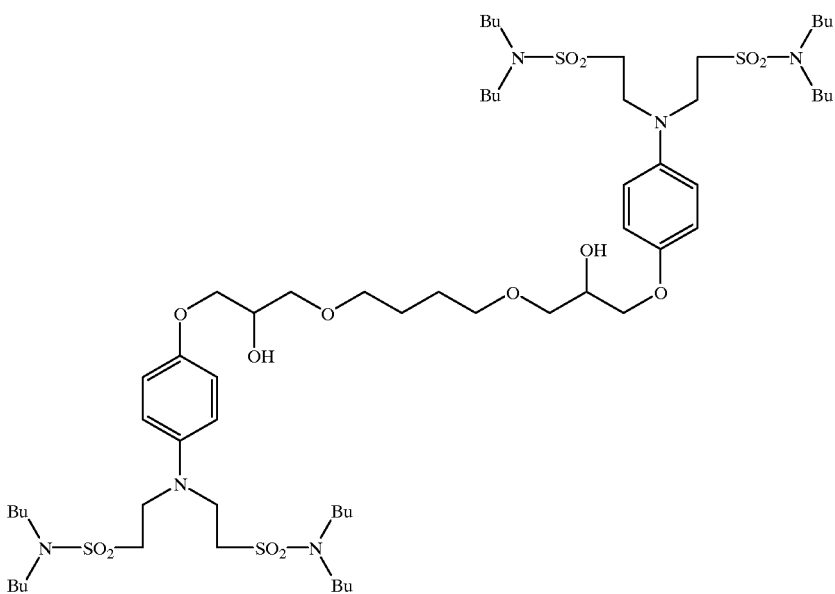
S-I-10
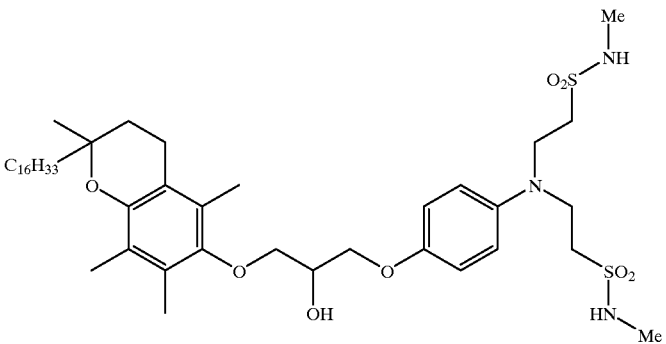
S-I-11
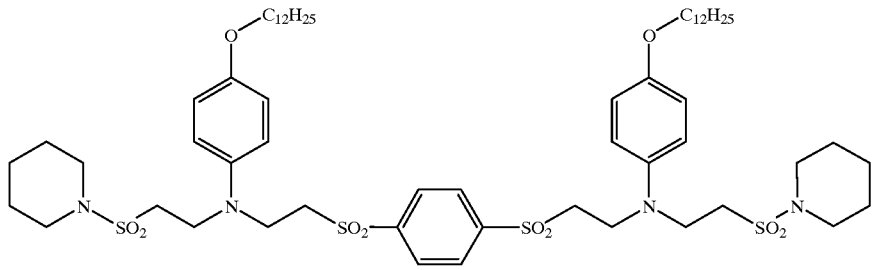

S-I-12
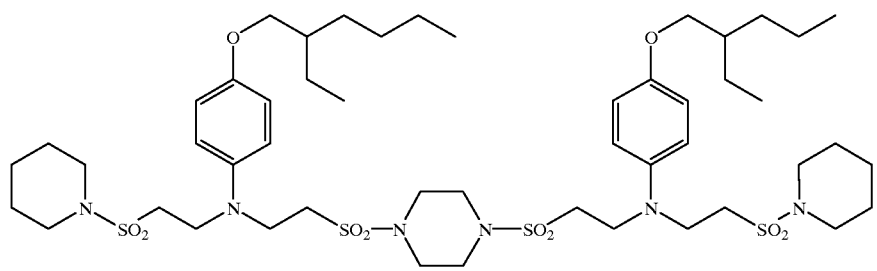
S-I-13
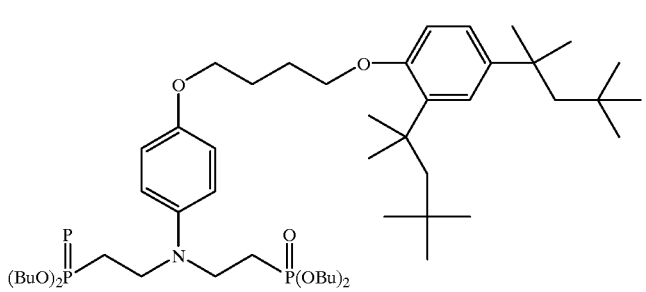
S-I-14
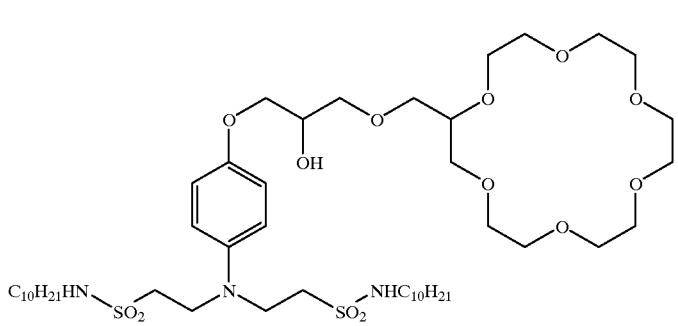
S-I-15
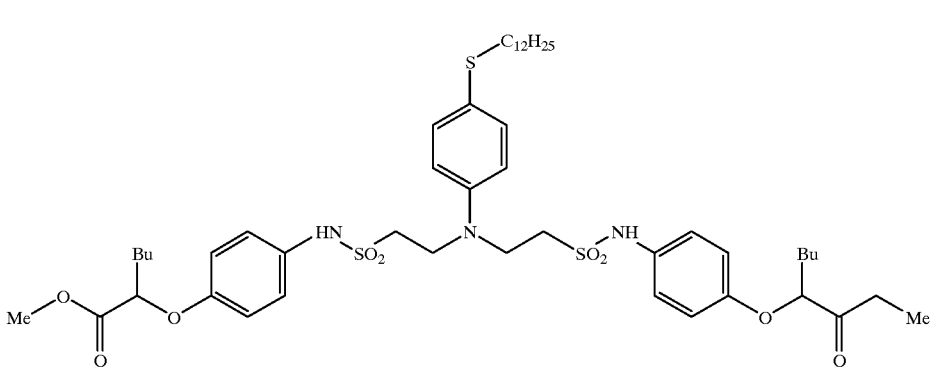
S-I-16
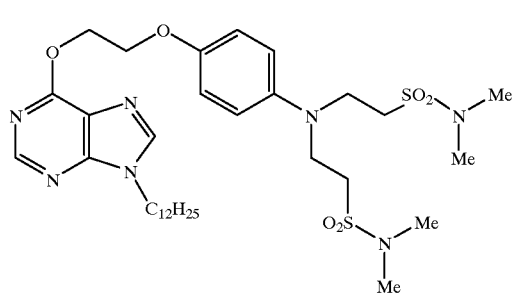

-continued

S-I-17

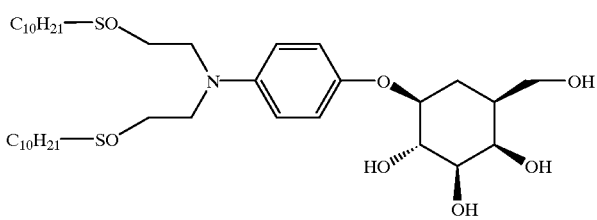

S-I-18

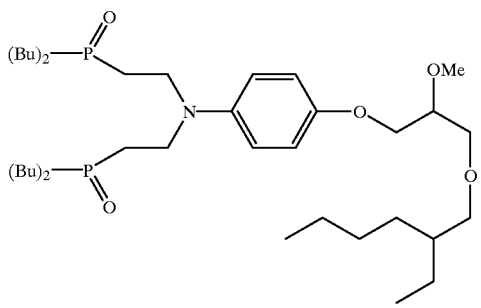

S-I-19

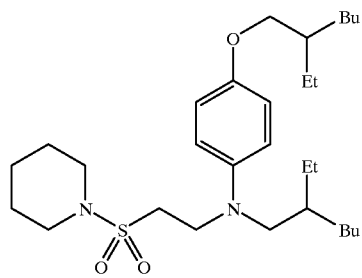

S-I-20

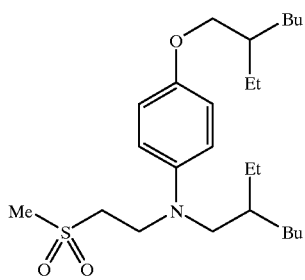

Compounds of formula S-I in accordance with the invention may be prepared using generally known synthetic techniques. It is a particular advantage of the invention that the independently disubstituted dialkylene amino substituents allow for more structural flexibility in comparison to the prior art thiomorpholine-1,1-dioxide type compounds. Preferred compounds in accordance with the invention comprising N,N-bis-ethane sulfonamides, e.g., may be prepared in accordance with the following synthetic scheme:

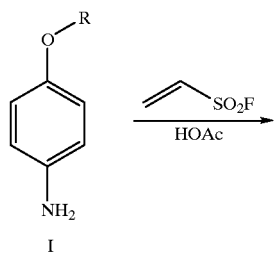

-continued

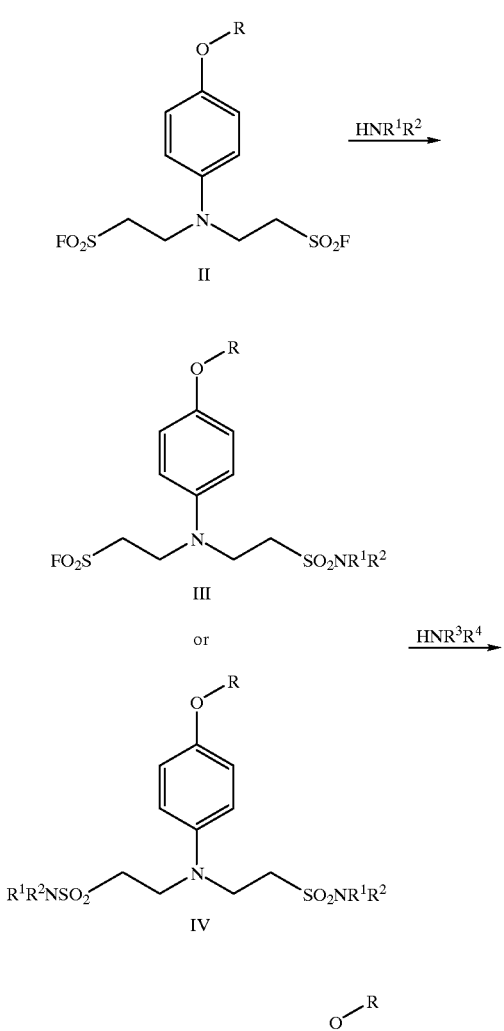

The Michael addition of alkoxyanilines (I) to vinyl sulfonyl fluoride affords the N,N-bis-ethane sulfonylfluorides (II) in good yield (J. J. Krutak, R. D. Burpitt, W. H. Moore and J. A. Hyatt, *J. Org. Chem.*, 44 (22), 3847 (1979)). Addition of amines to (II) can generate either the N-mono-ethane sulfonamides (III) or the symmetrical N,N-bis-ethane sulfonamides (IV) depending on the reaction conditions. Subsequent addition of a second amine to (III) affords the unsymmetrical N,N-bis-ethane sulfonamide (V).

Synthesis Example 1

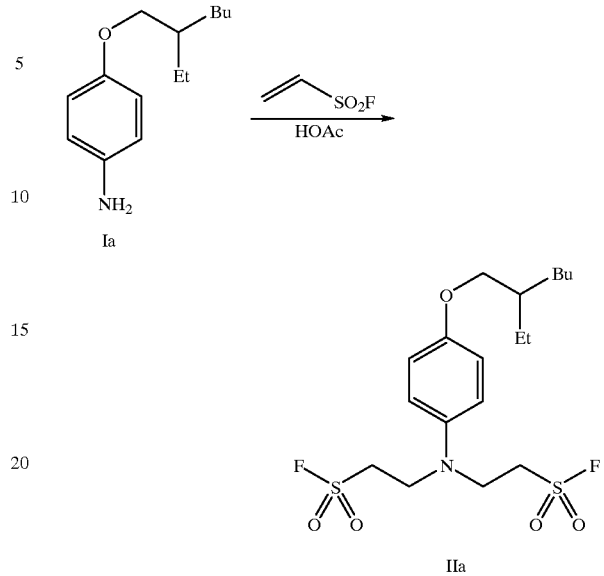

4-(2-Ethylhexaoxy)aniline (16.8 g, 75.9 mmol) was dissolved in acetic acid (40 ml) and vinylsulfonylfluoride (18.4 g, 167 mmol) was added dropwise. After approximately 2 hrs., the reaction mixture set-up to a solid mass. Additional acetic acid (15 ml) was added to aid stirring. After 1 hr. the solid was isolated by filtration and washed thoroughly with hexanes. Air drying afforded 25.8 g (77% yield) of the desired product, IIa, as a pale pink, crystalline solid, mp. 80–81° C.

Mass Spec.: FDMS($CDCl_3$)–m/e=441M.

NMR ($CDCl_3$): δ 6.9 (s, 4); 3.8 (m, 6); 3.4–3.6 (m, 4); 1.2–1.8 (m, 9); 0.8–1.0 (t, 6).

Compound S-I-2 (IVa)

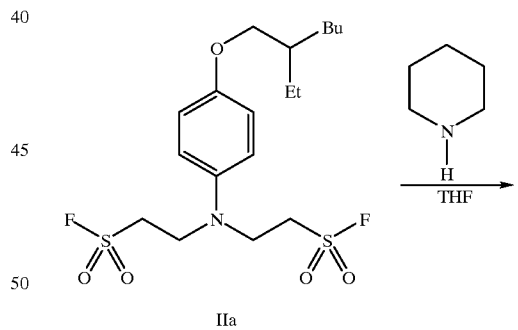

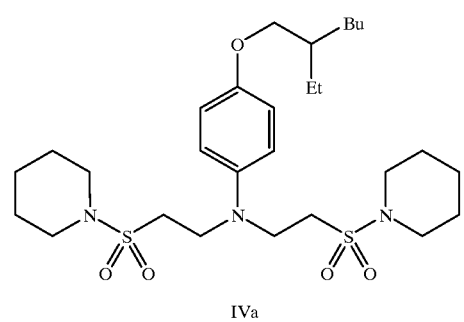

The above bis-ethanesulfonylfluoride (6.75 g, 15.3 mmol) and piperidine (6.51 g, 76.5 mmol) were combined in THF (100 ml) and heated at 45° C. for 18 hrs. The reaction was cooled, poured into ice water (500 ml) and acidified to pH=5–6 with acetic acid. After stirring for 2 hrs., the solid was isolated by filtration and washed with water. Air drying and recrystallization from isopropyl alcohol afforded 7.31 g (83% yield) of the desired product, IVa, as a white crystalline solid, mp 105–106° C.

Mass Spec.: FDMS(CDCl$_3$)–m/e=571M.

NMR (CDCl$_3$): δ 6.9 (d, 2); 6.75 (d, 2); 3.6–3.8 (m, 14); 3.2 (d, 8); 3.0–3.1 (t, 4); 1.2–1.8 (m, 9); 0.8 (t, 6).

Compound IIIb

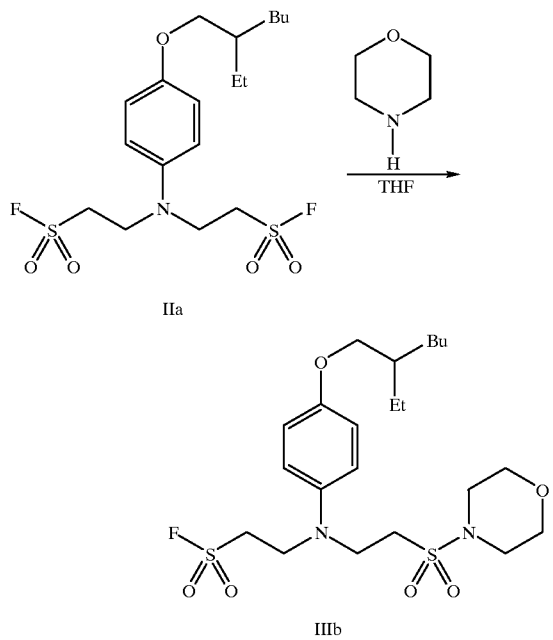

The bis-ethanesulfonylfluoride, IIa (1.94 g, 4.4 mmol) was dissolved in a minimal amount of THF and added dropwise to a solution of morpholine (2.5 g, 28.7 mmol) in THF (40 ml). After stirring overnight, an additional 0.5 ml of morpholine was added followed by a second portion of 1 ml after 7 hrs. After an additional 18 hrs., the reaction was poured into ice water and acidified to pH=5 with acetic acid. The mixture was extracted with CH$_2$Cl$_2$ (2x's) and the combined organic extracts were washed with brine (2x's), dried (Na$_2$SO$_4$) and freed of solvent under vacuum to afford 1.64 g of crude oil. This oil was combined with a previous run (2.4 g) and chromatographed on silica gel (2:98, acetone:CH$_2$Cl$_2$) to afford the mono-sulfonamide product, IIIb, as a tan colored oil, 0.93 g.

NMR (CDCl$_3$): δ 6.8 (d, 2); 6.85 (d, 2); 3.65–3.80 (m, 10); 3.55 (m, 2); 3.2 (t, 4); 3.05–3.1 (t, 2); 1.2–1.8 (m, 9); 0.8–0.95 (m, 6).

Compound S-I-4 (Vb)

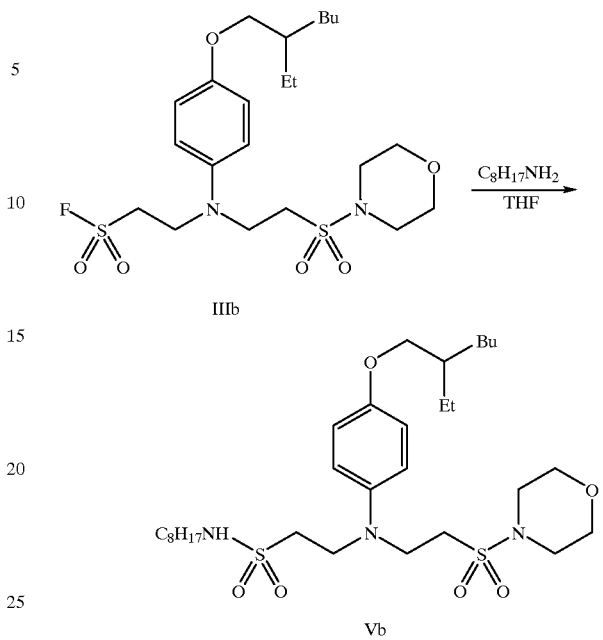

The above mono-sulfonamide, IIIb (0.93 g. 1.8 mmol) and $_n$-octylamine (0.7 g, 5.4 mmol) were dissolved in THF (10 ml) and heated to 40° C. for 24 hrs. A small amount of octylamine was added and the mixture heated an additional 24 hrs. The reaction was cooled and poured into ice water. Acidification with acetic acid to pH=5 afforded a tacky solid that was isolated by filtration, washed with water and dissolved in dichloromethane. The organic solution was washed with brine (2x's), dried (Na$_2$SO$_4$) and freed of solvent under vacuum. The crude oil (0.87 g) was chromatographed on silica gel (5:95, MeOH:CHCl$_3$) to afford 0.57 g of the desired product as white crystals; after recrystallization from isopropyl alcohol, mp=73–74.5° C.

Mass Spec: FDMS(CDCl3)–m/e=617M.

NMR (CDCl$_3$): δ 6.8–6.95 (m, 4); 5.1 (t, 1); 3.5–3.8 (m, 10); 3.1–3.3 (m, 8); 2.65–2.8 (m, 2); 1.05–1.8 (m, 21); 0.8–1.0 (t, 9).

The magenta dye forming coupler used in the elements in accordance with the invention is preferably a pyrazolone, pyrazolotriazole, or pyrazolobenzimidazole with or without a suitable leaving group. The magenta coupler can be monomeric, dimeric, trimeric, oligomeric or polymeric coupler wherein the coupler moiety can be attached to the polymeric backbone via a substituent on the coupler moiety or a substituent on a coupling off group. Illustrative magenta couplers are disclosed in, for example, U.S. Pat. Nos. 1,969,479; 2,311,082; 2,343,703; 2,369,489; 2,575,182; 2,600,788; 2,706,685; 2,908,573; 3,061,432; 3,062,653; 3,152,896; 3,153,816; 3,214,437; 3,253,924; 3,311,476; 3,419,391; 3,519,429; 3,725,067; 3,770,447; 3,907,571; 3,928,044; 3,935,015; 4,120,723; 4,123,281; 4,199,361; 4,336,325; 4,351,897; 4,385,111; 4,401,752; 4,407,936; 4,413,054; 4,283,472; 4,338,393; 4,420,556; 4,443,536; 4,500,630; 4,522,915; 4,540,654; 4,576,912; 4,581,326; 4,621,046; 4,728,598; 4,774,172; and 4,853,319 European Patent Applications Nos. 284,239; 284,240; 240,852; 170, 164; and 177,765; Japanese Patent Publication Nos. 60/170854, 60/194451 and 60/194452 and Great Britain Patents Nos. 1,047,612, 1,357,372 and 1,530,272, and "Farbkuppler-eine Literaturübersicht", published in Agfa Mitteilungen, Band III, pp 126–156 (1961); the disclosures of which are incorporated herein by reference.

Magenta dye-forming couplers may comprise pyrazolone compounds of the general formula:

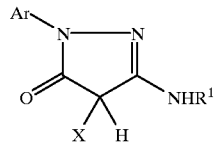

(M-I)

and

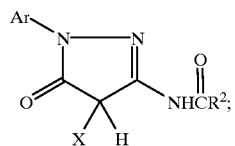

(M-II)

pyrazolotriazole compounds of the general formula:

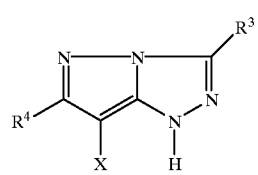

(M-III)

and

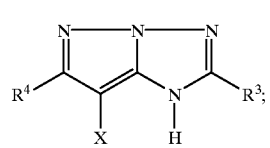

(M-IV)

and pyrazolobenzimidazoles of the formula:

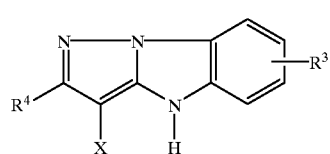

(M-V)

wherein

Ar is an unsubstituted aryl group or an aryl group (including pyridyl) substituted with one or more substituents selected from halogen atoms and cyano, alkylsulfonyl, arylsulfonyl, sulfamoyl, sulfonamido, carbamoyl, carbonamido, alkoxy, acyloxy, aryloxy, alkoxycarbonyl, aryloxycarbonyl, ureido, nitro, alkyl, and trifluoromethyl, or Ar is an aryl group substituted with a group which forms a link to a polymeric chain;

$R^1$ is a substituted or unsubstituted phenyl group and $R^2$ is a substituted or unsubstituted alkyl or phenyl group, the $R^1$ and $R^2$ substituents being individually selected from halogen atoms, and alkyl, aryl, alkoxy, aryloxy, carbonamido, carbamoyl, sulfonamido, sulfamoyl, alkylsulfinyl, arylsulfinyl, alkylsulfonyl, arylsulfonyl, alkoxycarbonyl, aryloxycarbonyl, acyl, acyloxy, ureido, imido, carbamate, heterocyclic, cyano, trifluoromethyl, alkylthio, nitro, carboxyl and hydroxyl groups, provided that $R^1$ and $R^2$ each contain at least 6 carbon atoms or the $R^1$ and $R^2$ substituents may individually comprise a group which forms a link to a polymeric chain;

$R^3$ and $R^4$ are individually selected from the group consisting of hydrogen, substituted and unsubstituted alkyl, substituted and unsubstituted phenyl, substituted and unsubstituted alkoxy, substituted and unsubstituted amino, substituted and unsubstituted anilino, substituted and unsubstituted acylamino, halogens and a group which links to a polymer, provided that the total number of carbon atoms contained in $R^3$ and $R^4$ is at least 6 if neither $R^3$ nor $R^4$ is a group which links to a polymer; and X is hydrogen or a coupling-off group selected from the group consisting of halogens, alkoxy, aryloxy, alkylthio, arylthio, acyloxy, sulfonamido, carbonamido, arylazo, nitrogen-containing heterocyclic and imido groups. Coupling-off groups are well known to those skilled in the photographic art. Generally, such groups determine the equivalency of the coupler and modify the reactivity of the coupler. Coupling-off groups can also advantageously effect the layer in which the coupler is coated or other layers in the photographic material by performing, after release from the coupler, such functions as development inhibition, bleach acceleration, color correction, development acceleration and the like. Representative coupling-off groups include, as noted above, halogens (for example, chloro), alkoxy, aryloxy, alkyl thio, aryl thio, acyloxy, sulfonamido, carbonamido, arylazo, nitrogen-containing heterocyclic groups such as pyrazolyl and imidazolyl, and imido groups such as succinimido and hydantoinyl groups. Except for the halogens, these groups may be substituted if desired. Coupling-off groups are described in further detail in: U.S. Pat. Nos. 2,355,169; 3,227,551; 3,432,521; 3,476,563; 3,617,291; 3,880,661; 4,052,212 and 4,134,766, and in British Patent References Nos. 1,466,728; 1,531,927; 1,533,039; 2,006,755A and 2,017,704A, the disclosures of which are incorporated herein by reference.

Magenta dye-forming couplers which contain bridgehead nitrogen 5,5 fused ring cyclic azoles systems are particularly suitable for use with the stabilizers of the invention. Such couplers include pyrazolotriazoles, pyrazolobenzimidazoles, and imidazopyrazoles and include such couplers as pyrrolo[1,2-b]pyrazoles, pyrazolo[3,2-c][1,2,4]triazoles, pyrazolo[2,3-b][1,2,4]triazoles, imidazo[1,2-b]pyrazoles, imidazo[1,5-b]pyrazoles, imidazo[1,2-a]imidazoles, imidazo[1,2-b][1,2,4]triazoles, imidazo[2,1-c][1,2,4]triazoles, imidazo[5,1-c][1,2,4]triazoles and [1,2,4]triazolo[3,4-c][1,2,4]triazole.

Specific couplers which may be used within the scope of the present invention include the following structures:

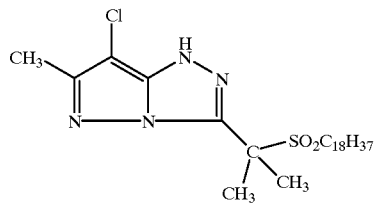
M-1
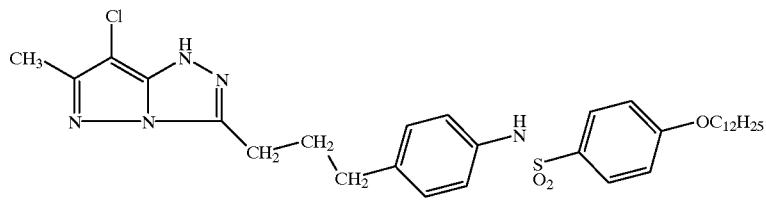
M-2
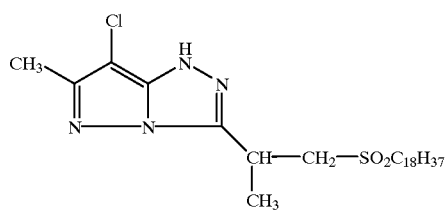
M-3
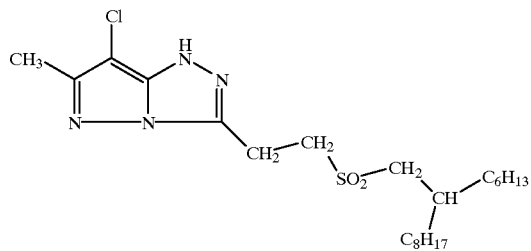
M-4
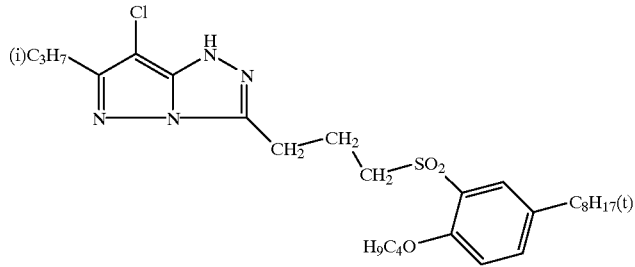
M-5
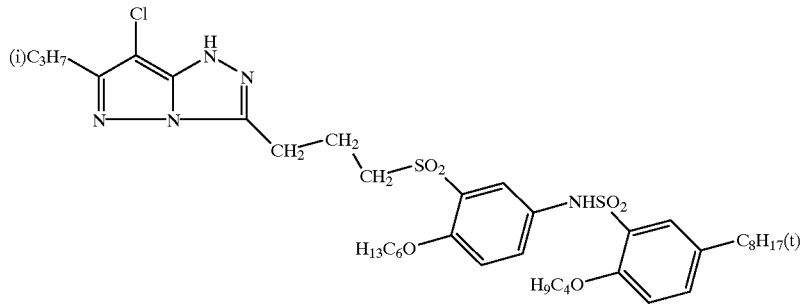
M-6

-continued
M-7
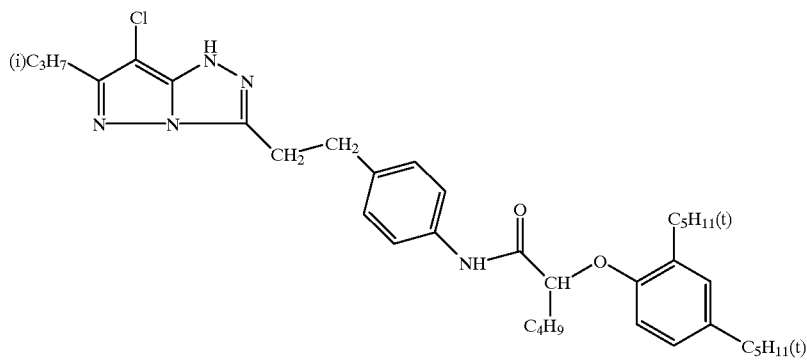
M-8
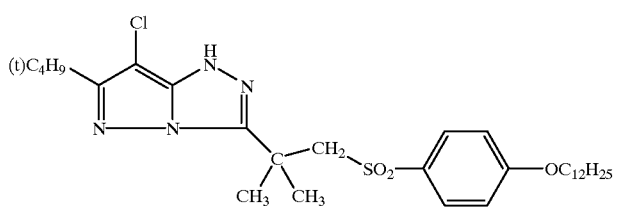
M-9
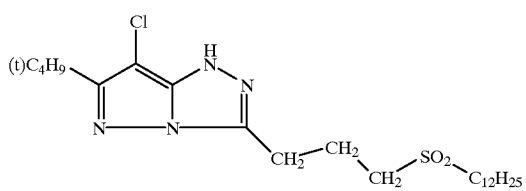
M-10
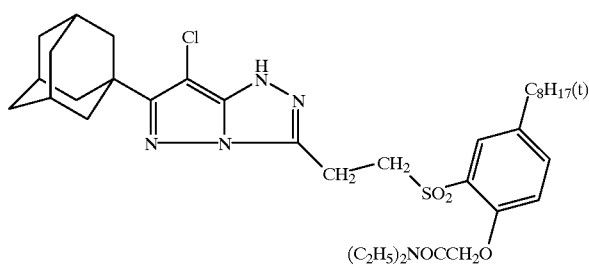
M-11
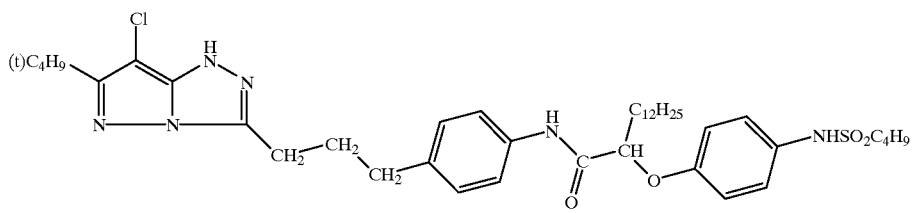
M-12
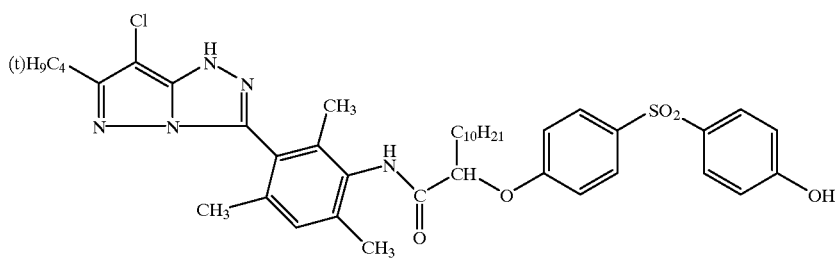

-continued
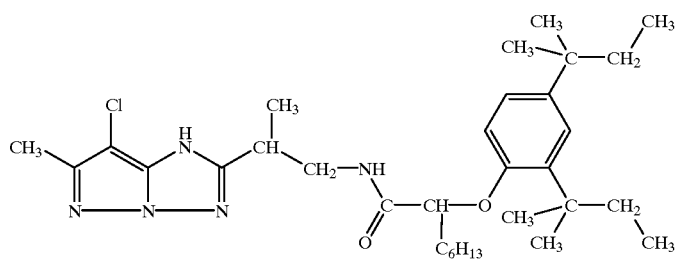
M-13
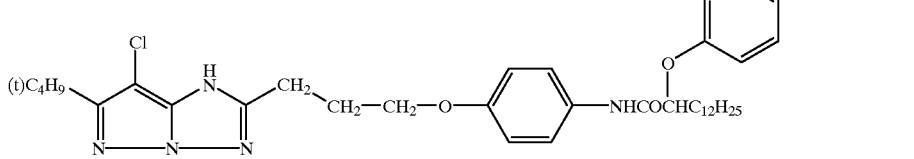
M-14
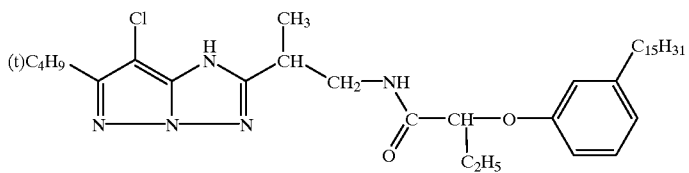
M-15
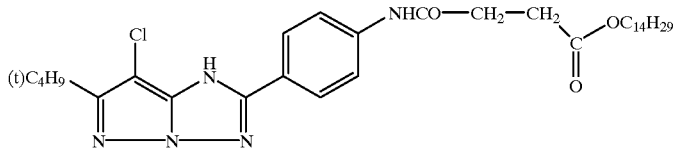
M-16
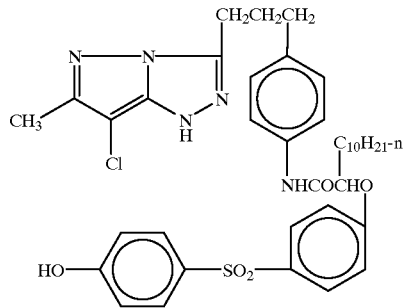
(M-17)
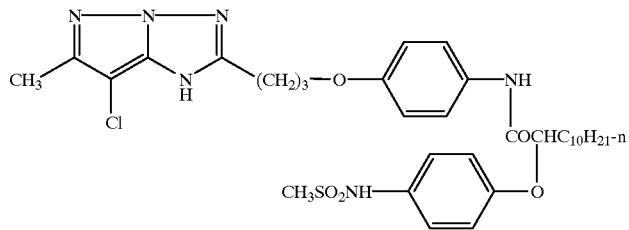
(M-18)

-continued
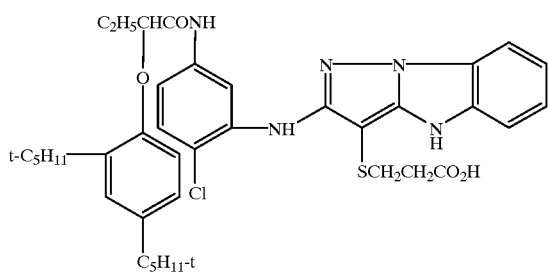
(M-19)
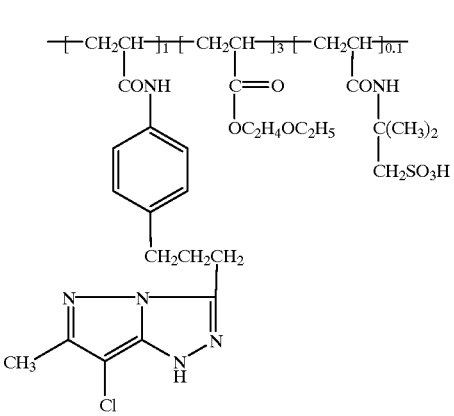
(M-20)
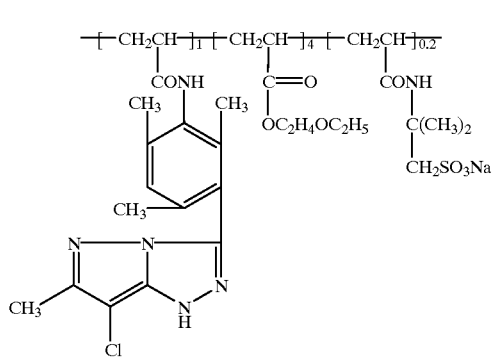
(M-21)
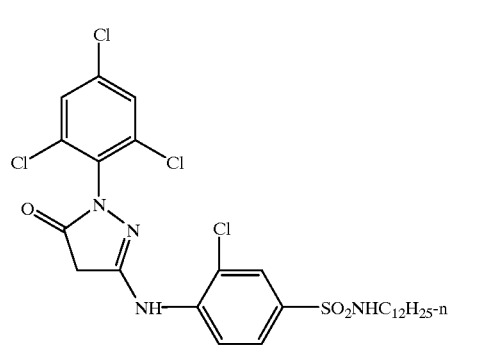
(M-22)

(M-23)
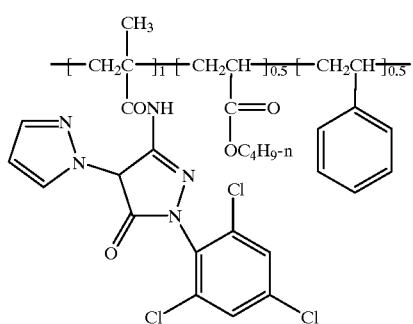
(M-24)
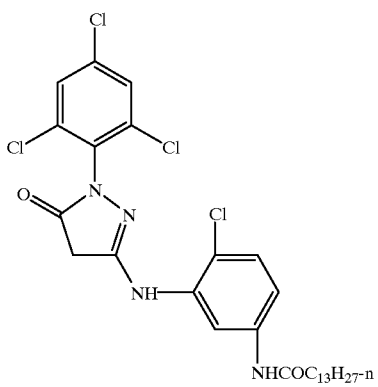
(M-25)
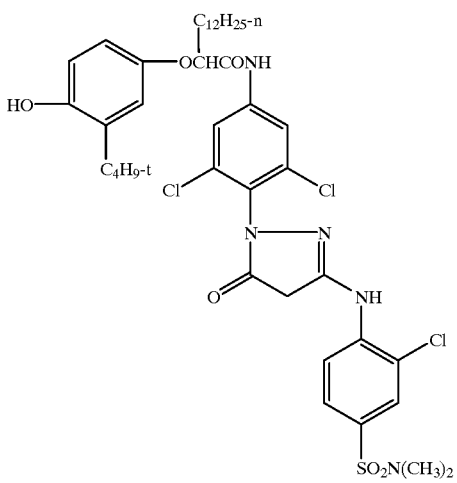
(M-26)
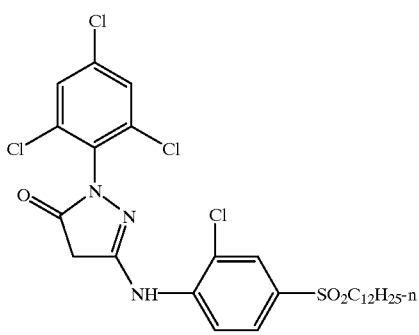

-continued
(M-27)
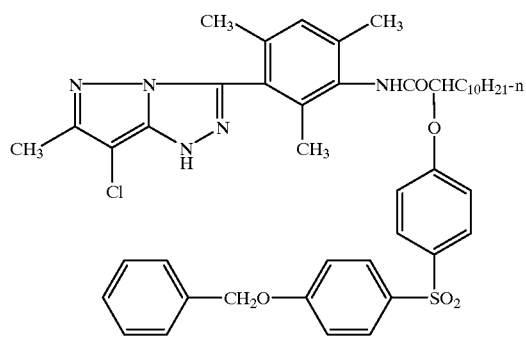
(M-28)
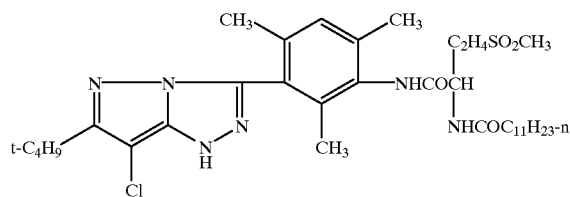
(M-29)
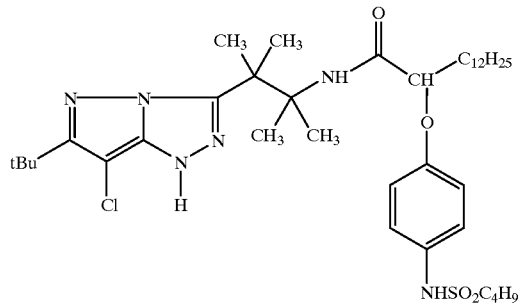
(M-30)
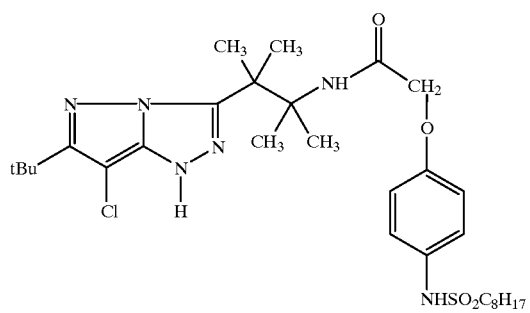
(M-31)
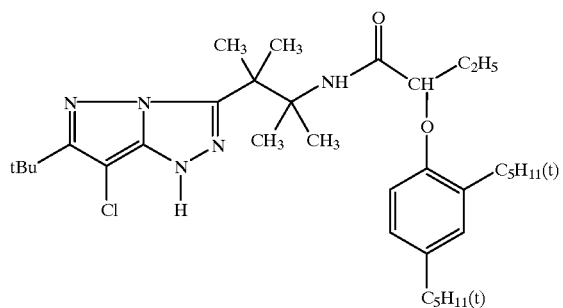

(M-32)

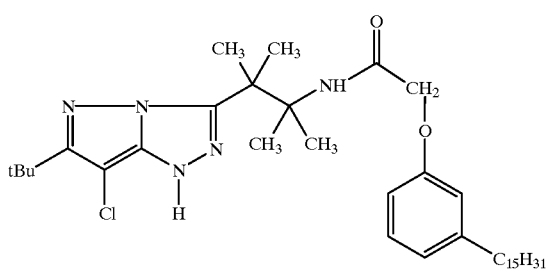

(M-33)

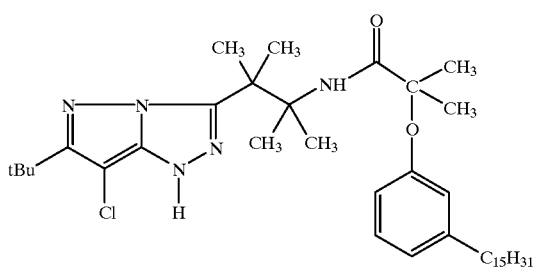

(M-34)

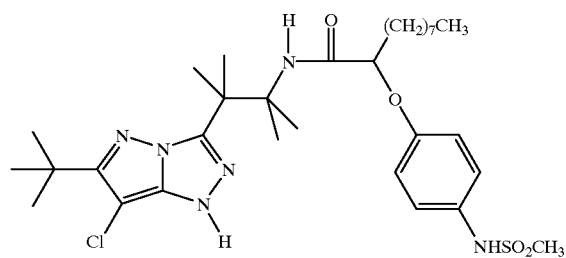

The coupler compounds of the present invention are known compounds and can be prepared by techniques known to those skilled in the art. References which describe the preparation of the magenta dye forming couplers are the patents and published applications referred to above as describing these compounds, and references cited therein.

Typically, the couplers and the stabilizers with which they are associated are dispersed in the same layer of the photographic element in a high boiling organic compound known in the art as a coupler solvent. Representative coupler solvents include phthalic acid alkyl esters such as diundecyl phthalate, dibutyl phthalate, bis-2-ethylhexyl phthalate, and dioctyl phthalate, phosphoric acid esters such as tricresyl phosphate, diphenyl phosphate, tris-2-ethylhexyl phosphate, and tris-3,5,5-trimethylhexyl phosphate, citric acid esters such as tributyl acetylcitrate, 2-(2-Butoxyethoxy)ethyl acetate, and 1,4-Cyclohexyldimethylene bis(2-ethylhexanoate), benzoic acid esters such as octyl benzoate, aliphatic amides such as N,N-diethyl lauramide, N,N-Diethyldodecanamide, N,N-Dibutyldodecanamide, mono and polyvalent alcohols such as oleyl alcohol and glycerin monooleate, and alkyl phenols such as p-dodecyl phenol and 2,4-di-t-butyl or 2,4-di-t-pentyl phenol. Commonly used coupler solvents are the phthalate esters, which can be used alone or in combination with one another or with other coupler solvents. Selection of the particular coupler solvent has been found to have an influence on the activity of the coupler as well as the hue and stability of the dye formed on coupling.

Typically the amount of compound S-I range from about 0.05 to about 2.0 moles stabilizer per mole of coupler, preferably from about 0.2 to 1.0 moles stabilizer per mole of coupler. The magenta coupler is typically coated in the element at a coverage of from 0.25 mmol/m$^2$ to 1.0 mmol/m$^2$, and preferably at a coverage of from 0.40 to 0.70 mmol/m$^2$. When a coupler solvent is employed, it typically is present in an amount of 0.1 to 5.0 mg/mg coupler, and preferably in an amount of 0.5 to 2.0 mg/mg coupler. To further enhance the stability of the dyes formed in photographic elements in accordance with the invention, additional conventional stabilizing compounds may also be included.

Throughout this application a reference to any type of chemical "group" includes both the unsubstituted and substituted forms of the group described. Generally, unless otherwise specifically stated, substituent groups usable on molecules herein include any groups, whether substituted or unsubstituted, which do not destroy properties necessary for the photographic utility. It will also be understood throughout this application that reference to a compound of a particular general formula includes those compounds of other more specific formula which specific formula falls within the general formula definition. Examples of substituents on any of the mentioned groups can include known substituents, such as: halogen, for example, chloro, fluoro, bromo, iodo; alkoxy, particularly those with 1 to 6 carbon atoms (for example, methoxy, ethoxy); substituted or unsubstituted alkyl, particularly lower alkyl (for example, methyl, trifluoromethyl); alkenyl or thioalkyl (for example, methylthio or ethylthio), particularly either of those with 1 to 6 carbon atoms; substituted and unsubstituted aryl, particularly those having from 6 to 20 carbon atoms (for example, phenyl); and substituted or unsubstituted heteroaryl, particularly those having a 5 or 6-membered ring containing 1 to 3 heteroatoms selected from N, O, or S (for example, pyridyl, thienyl, furyl, pyrrolyl); and others known in the art. Alkyl substituents may specifically include "lower alkyl", that is having from 1 to 6 carbon atoms, for example, methyl, ethyl, and the like. Further, with regard to any alkyl group, alkylene group or alkenyl group, it will be understood that these can be branched or unbranched and include ring structures.

The photographic elements of this invention can be black and white elements (for example, using magenta, cyan and yellow dye forming couplers), single color elements or multicolor elements. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

Photographic elements of this invention can have the structures and components shown on Research Disclosure, February 1995, Item 37038, pages 79–114. Research Disclosure is published by Kenneth Mason Publications, Ltd., Dudley Annex, 12a North Street, Emsworth, Hampshire PO10 7DQ, ENGLAND. Specific elements can be those shown on pages 96–98 of this Research Disclosure item as Color Paper Elements 1 and 2, in which is employed in the magenta dye forming layers the stabilizer combinations of the present invention instead of the stabilizers shown there. A typical multicolor photographic element of this invention comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like. All of these can be coated on a support which can be transparent or reflective (for example, a paper support). Photographic elements of the present invention may also usefully include a magnetic recording material as described in *Research Disclosure*, Item 34390, November 1992, or a transparent magnetic recording layer such as a layer containing magnetic particles on the underside of a transparent support as in U.S. Pat. Nos. 4,279,945 and 4,302,523. The element typically will have a total thickness (excluding the support) of from 5 to 30 microns. While the order of the color sensitive layers can be varied, they will normally be red-sensitive, green-sensitive and blue-sensitive, in that order on a transparent support, (that is, blue sensitive furthest from the support) and the reverse order on a reflective support being typical.

This invention also contemplates the use of photographic elements of the present invention in what are often referred to as single use cameras (or "film with lens" units). These cameras are sold with film preloaded in them and the entire camera is returned to a processor with the exposed film remaining inside the camera. Such cameras may have glass or plastic lenses through which the photographic element is exposed.

In the following discussion of suitable materials for use in elements of this invention, reference will be made to *Research Disclosure*, September 1994, Number 365, Item 36544, which will be identified hereafter by the term "Research Disclosure I." The Sections hereafter referred to are Sections of the Research Disclosure I.

The silver halide emulsions employed in the elements of this invention can be either negative-working, such as surface-sensitive emulsions or unfogged internal latent image forming emulsions, or direct positive emulsions of the unfogged, internal latent image forming type which are positive working when development is conducted with uniform light exposure or in the presence of a nucleating agent. Suitable emulsions and their preparation as well as methods of chemical and spectral sensitization are described in Sections I through V. Color materials and development modifiers are described in Sections V through XX. Vehicles which can be used in the elements of the present invention are described in Section II, and various additives such as brighteners, antifoggants, stabilizers, light absorbing and scattering materials, hardeners, coating aids, plasticizers, lubricants and matting agents are described, for example, in Sections VI through X and XI through XIV. Manufacturing methods are described in all of the sections, other layers and supports in Sections XI and XIV, processing methods and agents in Sections XIX and XX, and exposure alternatives in Section XVI.

With negative working silver halide a negative image can be formed. Optionally a positive (or reversal) image can be formed although a negative image is typically first formed.

The photographic elements of the present invention may also use colored couplers (e.g. to adjust levels of interlayer correction) and masking couplers such as those described in EP 213 490; Japanese Published Application 58-172,647; U.S. Pat. No. 2,983,608; German Application DE 2,706,117; U.K. Patent 1,530,272; Japanese Application A-113935; U.S. Pat. No. 4,070,191 and German Application DE 2,643, 965. The masking couplers may be shifted or blocked.

The photographic elements may also contain materials that accelerate or otherwise modify the processing steps of bleaching or fixing to improve the quality of the image. Bleach accelerators described in EP 193 389; EP 301 477; U.S. Pat. Nos. 4,163,669; 4,865,956; and 4,923,784 are particularly useful. Also contemplated is the use of nucleating agents, development accelerators or their precursors (UK Patent 2,097,140; U.K. Patent 2,131,188); electron transfer agents (U.S. Pat. Nos. 4,859,578; 4,912,025); anti-fogging and anti color-mixing agents such as derivatives of hydroquinones, aminophenols, amines, gallic acid; catechol; ascorbic acid; hydrazides; sulfonamidophenols; and non color-forming couplers.

The elements may also contain filter dye layers comprising colloidal silver sol or yellow and/or magenta filter dyes and/or antihalation dyes (particularly in an undercoat beneath all light sensitive layers or in the side of the support opposite that on which all light sensitive layers are located) either as oil-in-water dispersions, latex dispersions or as solid particle dispersions. Additionally, they may be used with "smearing" couplers (e.g. as described in U.S. Pat. No. 4,366,237; EP 096 570; U.S. Pat. Nos. 4,420,556; and 4,543,323.) Also, the couplers may be blocked or coated in protected form as described, for example, in Japanese Application 61/258,249 or U.S. Pat. No. 5,019,492.

The photographic elements may further contain other image-modifying compounds such as developer inhibitor releasing compounds (DIR's).

The elements of the present invention may be employed to obtain reflection color prints as described in *Research*

Disclosure, November 1979, Item 18716, available from Kenneth Mason Publications, Ltd, Dudley Annex, 12a North Street, Emsworth, Hampshire P0101 7DQ, England, incorporated herein by reference. The emulsions and materials to form elements of the present invention, may be coated on pH adjusted support as described in U.S. Pat. No. 4,917,994; with epoxy solvents (EP 0 164 961); with additional stabilizers (as described, for example, in U.S. Pat. Nos. 4,346, 165; 4,540,653 and 4,906,559); with ballasted chelating agents such as those in U.S. Pat. No. 4,994,359 to reduce sensitivity to polyvalent cations such as calcium; and with stain reducing compounds such as described in U.S. Pat. Nos. 5,068,171 and 5,096,805. Other compounds useful in the elements of the invention are disclosed in Japanese Published Patent Applications 83/09,959; 83/62,586; 90/072,629, 90/072,630; 90/072,632; 90/072,633; 90/072, 634; 90/077,822; 90/078,229; 90/078,230; 90/079,336; 90/079,338; 90/079,690; 90/079,691; 90/080,487; 90/080, 489; 90/080,490; 90/080,491; 90/080,492; 90/080,494; 90/085,928; 90/086,669; 90/086,670; 90/087,361; 90/087, 362; 90/087,363; 90/087,364; 90/088,096; 90/088,097; 90/093,662; 90/093,663; 90/093,664; 90/093,665; 90/093, 666; 90/093,668; 90/094,055; 90/094,056; 90/101,937; 90/103,409; 90/151,577.

The silver halide used in the photographic elements of the present invention may be silver iodobromide, silver bromide, silver chloride, silver chlorobromide, silver chloroiodobromide, and the like. The type of silver halide grains preferably include polymorphic, cubic, and octahedral. The grain size of the silver halide may have any distribution known to be useful in photographic compositions, and may be ether polydispersed or monodispersed. Particularly useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $T=ECD/t^2$ where ECD is the average equivalent circular diameter of the tabular grains in microns and t is the average thickness in microns of the tabular grains.

The average useful ECD of photographic emulsions can range up to about 10 microns, although in practice emulsion ECD's seldom exceed about 4 microns. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micron) tabular grains. To achieve the lowest levels of granularity it is preferred to that aim tabular grain projected areas be satisfied with ultrathin (t<0.06 micron) tabular grains. Tabular grain thicknesses typically range down to about 0.02 micron. However, still lower tabular grain thicknesses are contemplated. For example, Daubendiek et al. U.S. Pat. No. 4,672,027 reports a 3 mole percent iodide tabular grain silver bromoiodide emulsion having a grain thickness of 0.017 micron.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions tabular grains satisfying the stated thickness criteria above account for at least 70 percent of the total grain projected area. In the highest performance tabular grain emulsions tabular grains satisfying the thickness criteria above account for at least 90 percent of total grain projected area.

Suitable tabular grain emulsions can be selected from among a variety of conventional teachings, such as those of the following: *Research Disclosure*, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The silver halide grains to be used in the invention may be prepared according to methods known in the art, such as those described in *Research Disclosure I* and James, *The Theory of the Photographic Process*. These include methods such as ammoniacal emulsion making, neutral or acidic emulsion making, and others known in the art. These methods generally involve mixing a water soluble silver salt with a water soluble halide salt in the presence of a protective colloid, and controlling the temperature, pAg, pH values, etc, at suitable values during formation of the silver halide by precipitation.

The silver halide to be used in the invention may be advantageously subjected to chemical sensitization with noble metal (for example, gold) sensitizers, middle chalcogen (for example, sulfur) sensitizers, reduction sensitizers and others known in the art. Compounds and techniques useful for chemical sensitization of silver halide are known in the art and described in *Research Disclosure I* and the references cited therein.

The photographic elements of the present invention, as is typical, provide the silver halide in the form of an emulsion. Photographic emulsions generally include a vehicle for coating the emulsion as a layer of a photographic element. Useful vehicles include both naturally occurring substances such as proteins, protein derivatives, cellulose derivatives (e.g., cellulose esters), gelatin (e.g., alkali-treated gelatin such as cattle bone or hide gelatin, or acid treated gelatin such as pigskin gelatin), gelatin derivatives (e.g., acetylated g the like), and others as described in *Research Disclosure I*. Also useful as vehicles or vehicle extenders are hydrophilic water-permeable colloids. These include synthetic polymeric peptizers, carriers, and/or binders such as poly (vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers, and the like, as described in *Research Disclosure I*. The vehicle can be present in the emulsion in any amount useful in photographic emulsions. The emulsion can also include any of the addenda known to be useful in photographic emulsions. These include chemical sensitizers, such as active gelatin, sulfur, selenium, tellurium, gold, platinum, palladium, iridium, osmium, rhenium, phosphorous, or combinations thereof. Chemical sensitization is generally carried out at pAg levels of from 5 to 10, pH levels of from 5 to 8, and temperatures of from 30 to 80° C., as illustrated in *Research Disclosure*, June 1975, item 13452 and U.S. Pat. No. 3,772,031.

The silver halide may be sensitized by sensitizing dyes by any method known in the art, such as described in *Research Disclosure I*. The dye may be added to an emulsion of the silver halide grains and a hydrophilic colloid at any time prior to (e.g., during or after chemical sensitization) or simultaneous with the coating of the emulsion on a photographic element. The dye/silver halide emulsion may be mixed with a dispersion of color image-forming coupler immediately before coating or in advance of coating (for example, 2 hours).

Photographic elements of the present invention are preferably imagewise exposed using any of the known techniques, including those described in *Research Disclosure I*, section XVI. This typically involves exposure to light in the visible region of the spectrum, and typically such exposure is of a live image through a lens, although exposure can also be exposure to a stored image (such as a computer stored image) by means of light emitting devices (such as light emitting diodes, CRT and the like).

Photographic elements comprising the composition of the invention can be processed in any of a number of well-known photographic processes utilizing any of a number of well-known processing compositions, described, for example, in *Research Disclosure I*, or in T. H. James, editor, *The Theory of the Photographic Process*, 4th Edition, Macmillan, N.Y., 1977. In the case of processing a negative working element, the element is treated with a color developer (that is one which will form the colored image dyes with the color couplers), and then with a oxidizer and a solvent to remove silver and silver halide. In the case of processing a reversal color element, the element is first treated with a black and white developer (that is, a developer which does not form colored dyes with the coupler compounds) followed by a treatment to fog unexposed silver halide (usually chemical or light fogging), followed by treatment with a color developer. Preferred color developing agents are p-phenylenediamines. Especially preferred are: 4-amino-N,N-diethylaniline hydrochloride, 4-amino-3-methyl-N,N-diethylaniline hydrochloride, 4-amino-3-methyl-N-ethyl-N-(b-(methanesulfonamido)ethylaniline sesquisulfate hydrate, 4-amino-3-methyl-N-ethyl-N-(b-hydroxyethyl)aniline sulfate, 4-amino-3-b-(methanesulfonamido)ethyl-N,N-diethylaniline hydrochloride and 4-amino-N-ethyl-N-(2-methoxyethyl)-m-toluidine di-p-toluene sulfonic acid.

Development is followed by bleach-fixing, to remove silver or silver halide, washing and drying. Bleaching and fixing can be performed with any of the materials known to be used for that purpose. Bleach baths generally comprise an aqueous solution of an oxidizing agent such as water soluble salts and complexes of iron (III) (e.g., potassium ferricyanide, ferric chloride, ammonium or potassium salts of ferric ethylenediaminetetraacetic acid), water-soluble persulfates (e.g., potassium, sodium, or ammonium persulfate), water-soluble dichromates (e.g., potassium, sodium, and lithium dichromate), and the like. Fixing baths generally comprise an aqueous solution of compounds that form soluble salts with silver ions, such as sodium thiosulfate, ammonium thiosulfate, potassium thiocyanate, sodium thiocyanate, thiourea, and the like.

The stabilizers of this invention can be used in photographic elements that are intended to be processed in amplification processes that use developer/amplifier solutions described in U.S. Pat. No. 5,324,624, for example. When processed in this way, the low volume, thin tank processing system and apparatus described in U.S. patent application Ser. No. 08/221,711, filed Mar. 31, 1994, preferably is employed.

The following examples further illustrate this invention.
Singlet Oxygen Quenching Examples Photooxidation kinetics for compounds in accordance with the invention were determined with the use of a merry-go-round photochemical apparatus. The equipment is designed to photolyze multiple samples and/or concentrations simultaneously, insuring uniform radiation of all solutions. The light fade apparatus is equipped with a 500 watt tungsten-halogen light source that shines through a combination of filters onto a water jacketed beaker containing a merry-go-round sample holder. The function of the merry-go-round is to rotate the samples so that all solutions are exposed to the same amount of light regardless of possible nonuniformity of the light source or of the filter system. The lamp and filter system portion of the apparatus remain stationary during operation. Two photolysis units were constructed. The two units are identical with the exception that one is a single lamp unit while the other is equipped with an additional lamp and filter system for increased light intensity. The distance from the plane of light to the closest sample position is approximately 15 inches for the single lamp unit and approximately 3.5 inches for the double lamp unit. The double and single lamp units, as well as the distances, were selected to achieve intensities that permit convenient and practical irradiation times.

The apparatus can accommodate one sample holder, and holders with both 6 and 20 sample capacity are available. Sample holders that accommodate HPLC autosampler vials, as well as spectrophotometric cuvettes (1 cm pathlength) have been constructed. The samples are immersed in the water bath for temperature control. The filter holder is designed to hold multiple 6.5×6.5 inch glass filter plates, and combinations of appropriate filters allow for isolation of a narrow band of light if needed. All samples are rotated past the light source(s) at a constant rotation speed, and the entire volume of solution is exposed to the light source(s). A controller activates the light and the motion of the merry-go-round. The time of irradiation and the speed of rotation of the merry-go-round may be set by the user.

Methylene Blue, Rose Bengal, and 1,3-diphenylisobenzofuran (DPBF) were purchased from Aldrich Chemical Company. HPLC grade acetonitrile and methanol were obtained from J. T. Baker. All reagents were used without further purification. Solvents were bubbled with air for 15 minutes prior to use. Spectrophotometric measurements were determined with a Hewlett Packard HP8450a spectrophotometer.

The ability of compounds to act as quenchers of $^1O_2$ was determined by measuring its effect on the Methylene Blue-sensitized photooxidation of DPBF in methanol. In this system Methylene Blue is the sensitizer and DPBF is the acceptor. The photooxidation was followed by spectrophotometrically monitoring the decrease in DPBF absorption at 410 nm as a function of time. Solutions containing $2.2 \times 10^{-4}$ M Methylene Blue and $5.6 \times 10^{-5}$ M DPBF were irradiated at various times in the absence of stabilizer and in the presence of $2 \times 10^{-3}$ M and $5 \times 10^{-3}$ M stabilizer. Photolysis times ranged from 2 seconds to 10 minutes. The experiment used the single lamp fade unit and the 20-position merry-go-round cuvette holder. A 610 nm cutoff filter was employed to ensure that only the sensitizer absorbed the light. The entire experiment, including sample preparation, was conducted in the dark. A general reaction scheme mechanism for $^1O_2$ processes for this system is depicted in FIG. 1. The first step of the reaction scheme is absorption of light (hv) by the sensitizer to produce an excited state sensitizer ($^1$Sens). The quencher (Q) can in principle inhibit the reaction of the acceptor (A) by quenching singlet ($^1$Sens) or triplet ($^3$Sens) sensitizer, or by quenching or reacting with $^1O_2$. The excited singlet state ($^1$Sens) has a short lifetime and, therefore, quenching of the singlet is too inefficient to be of concern with most quenchers. The triplet state is generated by intersystem crossing (isc) and due to its longer lifetime it has a better chance to react. If the triplet sensitizer energy is greater than 22 kcal/mol, it can transfer energy to molecular oxygen generating singlet oxygen. Many singlet oxygen quenchers can interact with the excited triplet state of the sensitizer, thus decreasing the amount of $^1O_2$ generated.

The electronically excited $^1O_2$ molecules produced by energy transfer from triplet state sensitizer to molecular oxygen can exist in two excited states. The lower energy state, $^1\Delta_g$, (22 kcal/mol) is much longer lived and is believed to be the $^1O_2$ species which leads to reaction in solution. $^1O_2(^1\Delta_g)$ reactions comprise several pathways where chemical reactions and physical quenching are competitive processes. The rate constants ka, kd, and kq+kr represent the acceptor, solvent and stabilizer deactivation of $^1O_2$. The acceptor reaction with $^1O_2$ results in the formation of the oxidized product, $^1O_2$. The quencher is intended to inhibit the interactions of $^1O_2$ and acceptor. There are two types of processes by which the stabilizer can remove $^1O_2$ molecules. The first is physical quenching and the second is a destructive process termed chemical quenching. In addition solvent dependent radiationless decay of $^1O_2$ regenerates ground state oxygen.

The concentration of DPBF as a function of photolysis time was measured and the experimental data were fit by non-linear regression to obtain the first order rate constant (kobs) for the fade of DPBF. From the experimental absorbance vs time curves, it was possible to calculate the rates of DPBF disappearance in the absence and presence of quencher. Assuming that $^1O_2$ quenching is the only important inhibition (i.e. no quenching of sensitized excited states), then the following kinetic expression represents the photooxidation of the acceptor in the presence of quencher;

$$-d[A]/dt = K([A]/(kd/ka+[A]+kq/ka[Q]) \quad \text{Equation 1}$$

where K is proportional to the rate of singlet oxygen production and is constant for a constant concentration of sensitizer, and kq is the combined rate for physical and chemical quenching of $^1O_2$. The integrated form of Equation 1 was derived, and after substituting the experimentally determined kobs into the integrated expression, the ratio of the $^1O_2$ quenching rate constant (kq) and the acceptor reaction rate constant (ka) is given by $$kq/ka = (K-(A_0-A_{inf})(1-e^{-kobs})/\exists_A - \beta kobs)/[Q] \quad \text{Equation 2}$$

where $A_0$ is the initial absorbance, $\exists_A$ represents the extinction coefficient of DPBF (21,000 Lmol$^{-1}$ cm$^{-1}$), and the constant β defined as kd/ka is characteristic for a given acceptor in a known solvent. The constant K was determined from Equation 3 by following the decay rate of DPBF in the absence of quencher.

$$K = (A_0-A_{inf})(1-e^{-kobs})/\exists_A + \beta kobs \quad \text{Equation 3}$$

The final absorbance ($A_{inf}$) and all other values are known. The β value for the highly reactive chemical acceptor, DPBF, in methanol was determined by spectrophotometrically monitoring the Rose Bengal-sensitized photooxygenation reaction between DPBF and $^1O_2$. Five methanol solutions of DPBF, ranging in concentration from $2 \times 10^{-5}$ to $2 \times 10^{-4}$ M and containing identical quantities of Rose Bengal ($2.7 \times 10^{-4}$ M), were prepared in the dark. The solutions were irradiated for 10 seconds under identical conditions using the single lamp fade apparatus. Photolysis was carried out in disposable semimicro cuvettes at 23° C. The absorbance at 410 nm was recorded for each concentration of acceptor following photolysis.

In the absence of a $^1O_2$ quencher, $^1O_2$ either decays regenerating ground state oxygen, $^3O_2$, or reacts with colored acceptor (A) to form a colorless product ($AO_2$). The instantaneous quantum yield for product formation ($\emptyset_{AO_2}$) is $$\emptyset_{AO_2} = (\emptyset^3_{Sens})ka[A]/(kd+ka[A]) \quad \text{Equation 4}$$

where $\emptyset^3_{Sens}$ is the quantum yield of triplet sensitizer. At low acceptor concentration, ka[A]<kd and $\emptyset_{AO_2}$ is proportional to [A]. Substituting the constant β for kd/ka, the reciprocal of Equation 4 becomes $$1/\emptyset_{AO_2} = 1/\emptyset^3_{Sens}(1+\beta/[A]) \quad \text{Equation 5}$$

If the light flux is constant within a series of reactions then the amount of product formed in a given time of irradiation can be substituted since it is proportional to $\emptyset_{AO_2}$. A plot of the reciprocal of the product concentration vs the reciprocal of the mean acceptor concentration was fit by linear regression. The value of β was obtained from the slope/intercept ratio. This relationship is valid only if the acceptor concentration does not change appreciably during the reaction (negligible conversion).

The stability of compounds to singlet oxygen was determined in both methanol and acetonitrile. The dual lamp fade unit with a 610 nm cutoff filter was used to excite the sensitizer (Methylene Blue). Solutions containing $4.3 \times 10^{-5}$ M Methylene Blue and a single low stabilizer concentration ($1.5 \times 10^{-4}$ M) were irradiated for various times using the 6-position HPLC vial sample holder. The photolysis times ranged from 30 minutes to 8 hours. The disappearance of the stabilizer was monitored by HPLC employing a 100×2.1 mm HP Hypersil C-18 column with either a 0.1 M ammonium acetate/acetonitrile or a 0.1% TFA/acetonitrile gradient elution system. The relative reactivity of compounds with $^1O_2$ were determined by calculating the stabilizer half-life ($t_{1/2}$) in the presence of $^1O_2$.

Results for compounds S-I-1 through S-I-6, S-I-19 and S-I-20 in accordance with the invention and comparison compounds Comp-1 through Comp-7 evaluated as described above are given in Table I below:

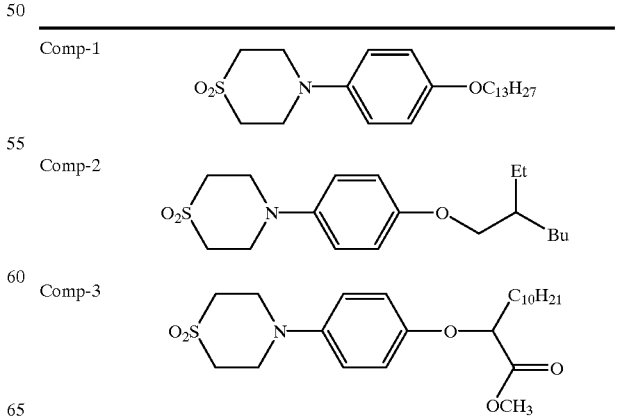

-continued

Comp-4
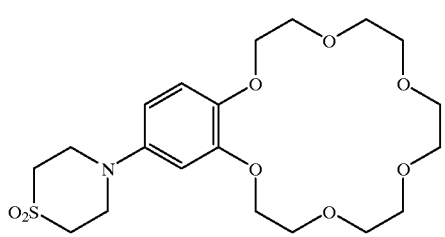

Comp-5
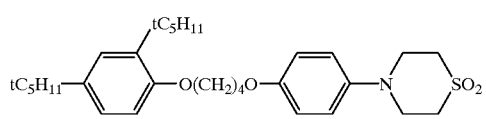

Comp-6
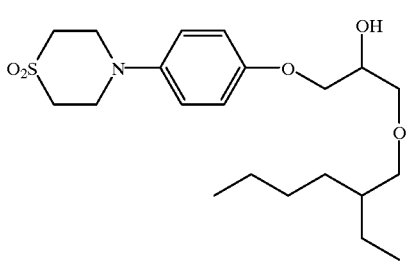

Comp-7
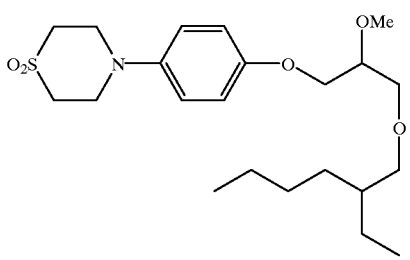

| Compound | $k_g k_a$ | $t_{1/2}$(MeCN) (hr) | Comments |
|---|---|---|---|
| S-I-1 | 0.3 | 3.7 | Invention |
| S-I-2 | 0.31 | 3.8 | Invention |
| S-I-3 | 0.28 | 3.2 | Invention |
| S-I-4 | 0.27 | 3.4 | Invention |
| S-I-5 | 0.2 | 2.4 | Invention |
| S-I-6 | 0.12 | 2.0 | Invention |
| S-I-19 | 0.39 | 1.3 | Invention |
| S-I-20 | 0.39 | 1.2 | Invention |
| Comp-1 | 0.18 | 2.6 | Comparison |
| Comp-2 | 0.19 | 3.0 | Comparison |
| Comp-3 | 0.12 | 3.0 | Comparison |
| Comp-4 | 0.22 | <0.5 | Comparison |
| Comp-5 | 0.13 | 3.1 | Comparison |
| Comp-6 | 0.22 | 2.2 | Comparison |
| Comp-7 | 0.15 | 2.4 | Comparison |

Compounds S-I-1 through S-I-6, S-I-19 and S-I-20 in accordance with the invention exhibit both good singlet oxygen quench rates and compound stability. Compounds S-I-1 through S-I-4 comprising sulfonamido $R^a$ and $R^b$ substituents with a combined σ* value of approximately 5.2 in accordance with preferred embodiments of the invention exhibit particularly good quench rates and compound stability in comparison to compounds Comp-1 through Comp-7.

Photographic Element Examples

Photographic elements were prepared with and without stabilizers of formula S-I (0, 0.017, 0.035, 0.069, 0.10, 0.17, or 0.26 g/m², corresponding to 0, 0.05, 0.1, 0.2, 0.3, 0.5 and 0.75 mol stabilizer/mol coupler) by coating the following layers in the order listed on a polyethylene-coated paper support:

| 1st layer | |
|---|---|
| Gelatin | 3.23 g/m² |
| 2nd layer | |
| Gelatin | 2.15 g/m² |
| Green sensitized AgCl emulsion | 0.17 g Ag/m² |
| Coupler M-9 | 0.29 g/m² |
| Dibutyl phthalate coupler solvent | 0.27 g/m² |
| Diethylhexyl phthalate coupler solvent | 0.27 g/m² |
| Stabilizer S-I-2 | 0–0.26 g/m² |
| Surfactant Alkanol XC (E. I. Dupont) | 0.26 g/m² |
| 3rd layer | |
| Gelatin | 1.40 g/m² |
| Bis(vinylsulfonyl)methane | 0.15 g/m² |
| Surfactants | 0.04 g/m² |

The photographic elements were given stepwise exposures to green light and processed at 35° C. as follows:

| Developer | 45 sec. |
|---|---|
| Bleach-Fix | 45 sec. |
| Wash (running water) | 1 min. 30 sec. |

The developer and bleach-fix had the following compositions:

| Developer | |
|---|---|
| Triethanolamine | 12.41 g |
| Blankophor REU ™ (Mobay Corp.) | 2.30 g |
| Lithium polystyrene sulfonate | 0.09 g |
| N,N-Diethylhydroxylamine | 4.59 g |
| Lithium sulfate | 2.70 g |
| N-{2-[(4-amino-3-methylphenyl)ethylamino]ethyl}methanesulfonamide sesquisulfate | 5.00 g |
| 1-Hydroxyethyl-1,1-diphosphonic acid | 0.49 g |
| Potassium carbonate, anhydrous | 21.16 g |
| Potassium chloride | 1.60 g |
| Potassium bromide | 7.00 mg |
| Water to make | 1.00 L |
| pH adjusted to 10.4 @ 26.7° C. | |
| Bleach-Fix | |
| Ammonium thiosulfate | 71.85 g |
| Ammonium sulfite | 5.10 g |
| Sodium metabisulfite | 10.00 g |
| Acetic acid (glacial) | 10.20 g |
| Ammonium ferric ethylenediaminetetraacetate | 48.58 g |
| Ethylenediaminetetraacetic acid | 3.86 g |
| Water to make | 1.00 L |
| pH adjusted to 6.7 @ 26.7° C. | |

Magenta dyes were formed upon processing. The density of each strip was measured. The strips were then covered by UV-absorbing filters (in lieu of coating a similar filter layer over the photosensitive layer of the elements) and subjected to irradiation by the light of a xenon arc lamp at an intensity of 50 klux for two weeks. Photographic elements containing stabilizer compound S-I-2 in accordance with the invention showed significantly improved light stability of the magenta dye as evidenced by the density to green light remaining from an initial density of 1.0 in comparison to the element containing no S-I-2.

A specific embodiment of the invention is a multilayer element provided on a reflective support and employing silver chloride emulsions and coated as taught in Research

*Disclosure*, September 1996, Item 38957 which is exemplified by the following:

| Coating Format | Laydown mg/m$^2$ |
|---|---|
| Layer Blue Sensitive Layer | |
| Gelatin | 1300 |
| Blue sensitive silver | 640 |
| Yellow Coupler Y-1 | 440 |
| St-3 | 440 |
| S-1 | 190 |
| Layer Interlayer | |
| Gelatin | 650 |
| Sc-1 | 55 |
| S-1 | 160 |
| Layer Green Sensitive Layer | |
| Gelatin | 1100 |
| Green sensitive silver | 70 |
| Magenta Coupler M-29 | 270 |
| S-1 | 75 |
| S-2 | 32 |
| St-1 | 20 |
| S-I-2 | 165 |
| St-2 | 530 |
| Layer UV Interlayer | |
| Gelatin | 635 |
| UV-1 | 30 |
| UV-2 | 160 |
| Sc-1 | 50 |
| S-3 | 30 |
| S-1 | 30 |
| Layer Red Sensitive Layer | |
| Gelatin | 1200 |
| Red sensitive silver | 170 |
| Cyan Coupler C-1 | 365 |
| S-1 | 360 |
| UV-2 | 235 |
| S-4 | 30 |
| Sc-1 | 3 |
| Layer UV Overcoat | |
| Gelatin | 440 |
| UV-1 | 20 |
| UV-2 | 110 |
| Sc-1 | 30 |
| S-3 | 20 |
| S-1 | 20 |
| Layer SOC | |
| Gelatin | 490 |
| Sc-1 | 17 |
| SiO$_2$ | 200 |
| Surfactant | 2 |

Y-1

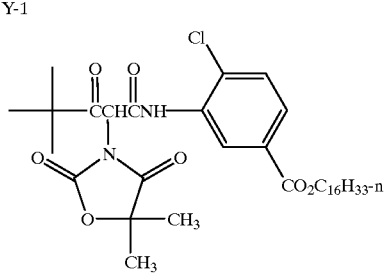

M-29

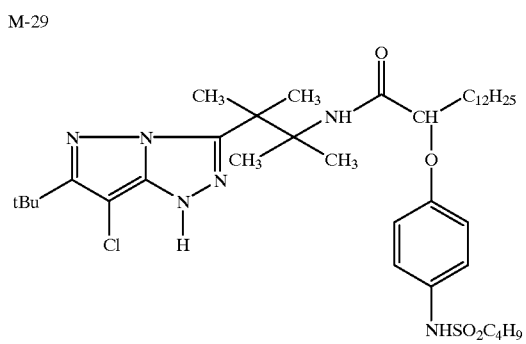

C-1

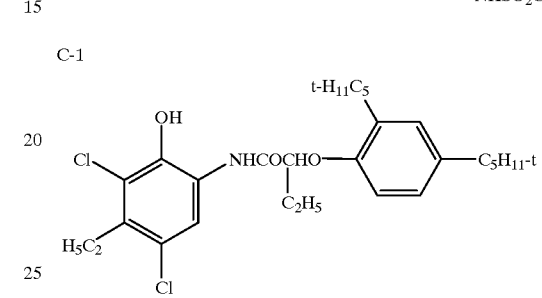

S-1

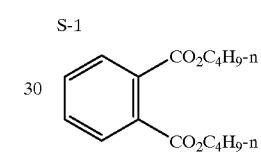

S-2

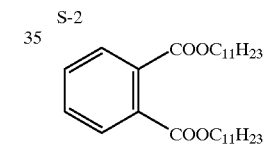

S-3

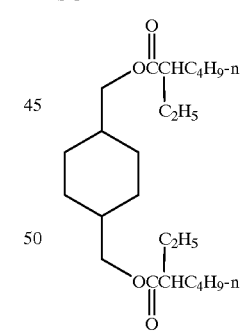

S-4   $CH_3COOC_2H_4OC_2H_4OC_4H_9$

Sc-1

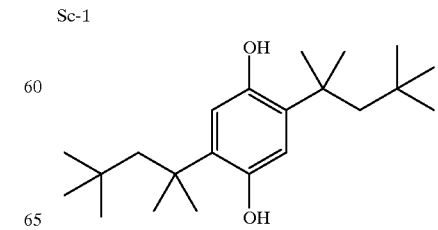

-continued

St-1

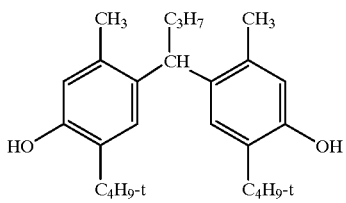

St-2

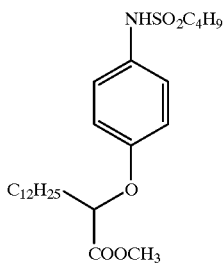

St-3  N-t-butyl(acrylamide)/n-butyl acrylate copolymer(50:50)

UV-1

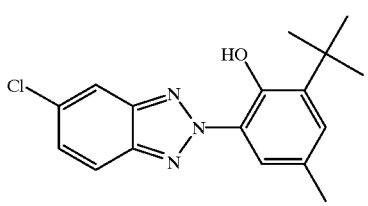

UV-2

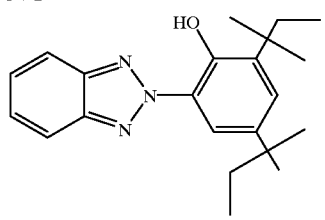

The invention has been described by reference to preferred embodiments, but it will be understood changes can be made to the embodiments specifically described herein within the spirit and scope of the invention.

What is claimed is:

1. A photographic element comprising a silver halide emulsion layer having associated therewith a magenta coupler and a magenta dye stabilizer compound of the formula:

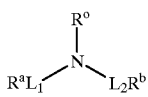

wherein
$R^o$ represents an aryl group or a heterocyclic group;
$L_1$ and $L_2$ are independently linear alkylene or cycloalkylene linking groups; and
$R^a$ and $R^b$ are independently selected substituent groups at least one of which has a $\sigma^*$ value of at least 1.8, wherein at least one of $R^a$ and $R^b$ is selected from sulfamoyl, sulfonyl, sulfinyl, phosphonyl, phosphinyl, perfluorinated alkyl, and perfluorinated thio groups.

2. An element according to claim 1, wherein the stabilizer compound is of the formula

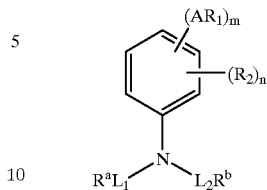

wherein
m is 1, 2, 3 or 4;
n is 0, 1, 2, 3, or 4, provided that the sum of m and n is less than or equal to 5;
A is $-NR_1'-$, $-S-$, or $-O-$;
$R_1$ and $R_1'$ are independently H or a substituent group and $R_2$ is a substituent group, provided that substituent groups represented by $R_1$ and $R_2$ or two $R_1$ or $R_2$ groups may be joined to form a ring.

3. An element according to claim 2, wherein the stabilizer compound is of the formula:

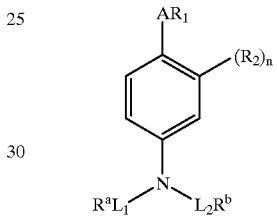

wherein n is 0 or 1.

4. An element according to claim 3 wherein A is $-O-$.

5. An element according to claim 3 wherein $R^a$ and $R^b$ are independently selected substituent groups each of which has a $\sigma^*$ value of at least 1.8.

6. An element according to claim 3 wherein the combined $\sigma^*$ value for $R^a$ and $R^b$ is from 3.6 to 7.2.

7. An element according to claim 6 wherein the combined $\sigma^*$ value for $R^a$ and $R^b$ is from 4.5 to 6.0.

8. An element according to claim 7 wherein each of $L_1$ and $L_2$ represents an ethylene linking group.

9. An element according to claim 8 wherein each of $R^a$ and $R^b$ is of the formula

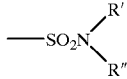

wherein R' and R" are independently selected from the group consisting of H, alkyl and aryl groups.

10. An element according to claim 1 wherein $R^a$ and $R^b$ are independently selected substituent groups each of which has a $\sigma^*$ value of at least 1.8.

11. An element according to claim 1 wherein $R^a$ and $R^b$ are independently selected substituent groups at least one of which has a $\sigma^*$ value of at least 2.5.

12. An element according to claim 1 wherein $R^a$ and $R^b$ are independently selected substituent groups each of which has a $\sigma^*$ value of at least 2.5.

13. An element according to claim 1 wherein the combined $\sigma^*$ value for $R^a$ and $R^b$ is from 3.6 to 7.2.

14. An element according to claim 1 wherein the combined $\sigma^*$ value for $R^a$ and $R^b$ is from 4.5 to 6.0.

15. An element according to claim 1 wherein $L_1$ and $L_2$ are selected from alkylene groups having the formula —(C(R)(R))p—, where p equals 1, 2 or 3 and each R may be independently H or an alkyl group, or two R alkyl groups may be joined to form a cycloalkylene ring.

16. An element according to claim 15 wherein p equals 2.

17. An element according to claim 1 wherein each of $L_1$ and $L_2$ represents an ethylene linking group.

18. An element according to claim 1 wherein at least one of $R^a$ and $R^b$ is of the formula

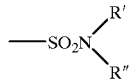

wherein R' and R" are independently selected from the group consisting of H, alkyl and aryl groups.

19. An element according to claim 18, wherein each of $R^a$ and $R^b$ is of the formula

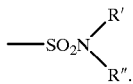

* * * * *